US006955814B1

(12) United States Patent
Dobson

(10) Patent No.: US 6,955,814 B1
(45) Date of Patent: Oct. 18, 2005

(54) ORGAN ARREST, PROTECTION AND PRESERVATION

(75) Inventor: Geoffrey Phillip Dobson, Wulguru (AU)

(73) Assignee: Global Cardiac Solutions PTY Ltd., Queensland (AU)

( * ) Notice: Subject to any disclaimer, the term of this patent is extended or adjusted under 35 U.S.C. 154(b) by 0 days.

(21) Appl. No.: 09/937,181

(22) PCT Filed: Mar. 22, 2000

(86) PCT No.: PCT/AU00/00226

§ 371 (c)(1),
(2), (4) Date: Jan. 10, 2002

(87) PCT Pub. No.: WO00/56145

PCT Pub. Date: Sep. 28, 2000

(30) Foreign Application Priority Data

Mar. 23, 1999 (AU) .............................................. PP9414
Nov. 23, 1999 (AU) .............................................. PQ4199

(51) Int. Cl.[7] ............................ A61K 9/00; A61K 33/00
(52) U.S. Cl. ........................ 424/400; 424/600; 436/18
(58) Field of Search ................................ 424/400, 600; 435/1.1, 325, 324; 436/18

(56) References Cited

U.S. PATENT DOCUMENTS

| 4,798,824 A | | 1/1989 | Belzer et al. |
| 5,145,771 A | | 9/1992 | Lemasters et al. |
| 5,206,222 A | | 4/1993 | Forman et al. |
| 5,256,770 A | * | 10/1993 | Glasser et al. |
| 5,370,989 A | | 12/1994 | Stern et al. |
| 5,407,793 A | | 4/1995 | Del Nido et al. |
| 5,432,053 A | | 7/1995 | Berdyaev et al. |
| 5,693,462 A | * | 12/1997 | Raymond |
| 6,187,615 B1 | | 2/2001 | Kim et al. |
| 6,187,756 B1 | | 2/2001 | Lee et al. |
| 6,569,615 B1 | | 5/2003 | Thatte et al. |

FOREIGN PATENT DOCUMENTS

| SU | 0878297 | 7/1981 |
| WO | WO 92/20346 | 11/1992 |
| WO | WO 98/37886 | 9/1998 |
| WO | WO 00/03716 | 1/2000 |

OTHER PUBLICATIONS

Koh Takeuchi et al. "Prolonged Preservation of the Blood--Perfused Canine Heart With Glycolysis-Promoting Solution", Society of Thoracic Surgeons, (1999) 903–907.

Hicks et al., "ATP-Sensitive Potassium Channel Activation Mimics the Protective Effect of Ischaemic Preconditions in the Rat Isolated Working Heart After Prolonged Hypothermic Storage" *Clinical and Experimental Pharmacology and Physiology* 26:20–25 (1999).

Forman et al., "Adenosine therapy at reperfusion on myocardial infarct size," *Cardiovascular Research* 33:497–498 (1997).

Garratt et al., "Intravenous adenosine and lidocaine in patients with acute myocardial infarction," *American Heart Journal* 136(2):196–204 (Aug. 1998).

Mahaffey et al., "Adenosine as an adjunct to Thrombolytic therapy for acute myocardial infarction," *JACC* 34(6):1711–20 (Nov. 1999).

Homeister et al., "Combined Adenosine and Lidocaine Administration Limits Myocardial Reperfusion Injury," *Circulation*, 82(2):595–608 (Aug. 1990).

Vander Heide et al., "Adenosine therapy at reperfusion and myocardial infarct size," *Cardiovascular Research*, 33:499–500 (1997).

Jayawant et al., "Advantages of continuous hyperpolarized arrest with pinacidil over St. Thomas Hospital solution during prolonged eschemia" *J. Thoracic and Cardiovascular Surgery*, 11(1):131–138 (1998).

Canyon, Sarah J. and Dobson, Geoffrey P., "Protection against ventricular arrhythmias and cardiac death using adenosine and lidocaine during regional ischemia in the in vivo rat," *Am J Physiol Heart Circ Physiol* 287:H1286–H1295 American Physiological Society (2004).

Dobson, Geoffrey P., "Organ arrest, protection and preservation: natural hibernation to cardiac surgery," *Comparative Biochemistry and Physiology*, Part B 139:469–485, Elsevier Inc. (2004).

Dobson, Geoffrey P., and Jones, Michael W., "Adenosine and lidocaine: A new concept in nondepolarizing surgical myocardial arrest, protection, and preservation," The Journal of Thoracic and Cardiovascular Surgery 127:794–805 (Mar. 2004).

* cited by examiner

*Primary Examiner*—Leon B. Lankford, Jr.
*Assistant Examiner*—Ruth A. Davis
(74) *Attorney, Agent, or Firm*—Venable LLP; Michael A. Gollin

(57) ABSTRACT

The present invention relates to a method for arresting, protecting and/or preserving an organ which includes administering effective amounts of (I) a potassium channel opener or agonist and/or an adenosine receptor agonist and (II) local anaesthetic to a subject in need thereof. The present invention also relates to a method for arresting, protecting and/or preserving an organ which comprises adding a composition which includes effective amounts of (I) a potassium channel opener or agonist and/or an adenosine receptor agonist and (II) a local anaesthetic to the organ. The present invention further provides a pharmaceutical or veterinary composition which includes effective amounts of (I) a potassium channel opener or agonist and/or an adenosine receptor agonist and (II) a local anaesthetic.

21 Claims, 15 Drawing Sheets

ORGAN ARREST, PROTECTION AND PRESERVATION

The present invention relates to a method and pharmaceutical or veterinary composition for arresting, protecting and/or preserving organs, in particular the heart during open-heart surgery, cardiovascular diagnosis or therapeutic intervention.

There are over 20,000 open-heart surgery operations each year in Australia, over 800,000 in the United States and about 1,000,000 in Europe. Of those requiring open-heart surgery, about 1.2% are neonates/infants primarily as a consequence of congenital heart disease.

The heart may be arrested for up to 3 hours during open-heart surgery. High potassium cardioplegia (in excess of 15–20 mM) has been the basis of myocardial arrest and protection for over 40 years. Currently the majority of solutions used contain high potassium including the widely used St Thomas No. 2 Hospital Solution which generally contains 110 mM NaCl, 16 mM KCl, 16 mM $MgCl_2$, 1.2 mM $CaCl_2$ and 10 mM $NaHCO_3$ and has a pH of about 7.8. High potassium solutions usually lead to a membrane depolarisation from about −80 to −50 mV. Notwithstanding hyperkalemic solutions providing acceptable clinical outcomes, recent evidence suggests that progressive potassium induced depolarisation leads to ionic and metabolic imbalances that may be linked to myocardial stunning, ventricular arrhythmias, ischaemic injury, endothelial cell swelling, microvascular damage, cell death and loss of pump function during the reperfusion period. Infant hearts are even more prone to damage with cardioplegic arrest from high potassium than adult hearts. The major ion imbalances postulated are linked to an increased sodium influx which in turn activates the $Na^+/Ca^{2+}$ exchangers leading to a rise in intracellular $Ca^{2-}$ Compensatory activation of $Na^+$ and $Ca^{2+}$ ion pumps then occur, which activate anaerobic metabolism to replenish ATP with a concomitant increase in tissue lactate and fall in tissue pH. Free radical generation and oxidative stress have also been implicated in potassium arrest and partially reversed by the administration of antioxidants. In some cases high potassium induced ischaemia has been reported to have damaged smooth muscle and endothelial function.

In an attempt to minimise ischaemic damage during cardioplegic arrest, an increasing number of experimental studies have employed potassium channel openers instead of high potassium. Cardioprotection using nicorandil, aprikalim or pinacidil is believed to be linked to the opening of the potassium channel which leads to a hyperpolarised state, a shortening of the action potential and decreasing $Ca^{2+}$ influx into the cell. One shortfall however is that the heart takes the same time or longer to recover with no improvement in function than with high potassium cardioplegic solutions. Another limitation is that pinacidil requires a carrier due to its low solubility in aqueous solutions. The carrier routinely used is dimethyl sulphoxide (DMSO) which is controversial when used in animal or human therapy.

Most investigators, including those who advocate using potassium channel openers, believe that as soon as blood flow is halted and the arrest solution administered, ischaemia occurs and progressively increases with time. To reduce the likelihood of damage, we sought a cardioplegic solution that would place the heart in a reversible hypometabolic state analogous to the tissues of a hibernating turtle, a hummingbird in torpor or an aestivating desert frog. When these animals drop their metabolic rate (some by over 90%), their tissues do not become progressively ischaemic but remain in a down-regulated steady state where supply and demand are matched. An ideal cardioplegic solution should produce a readily reversible, rapid electrochemical arrest with minimal tissue ischaemia. The heart should accumulate low tissue lactate, utilise little glycogen, show minimal changes in high-energy phosphates, cytosolic redox (NAD/NADH) and the bioenergetic phosphorylation (ATP/ADP Pi) ratio and free energy of ATP. There should be little or no change in cytosolic pH or free magnesium, minimal water shifts between the intracellular and extracellular phases, and no major ultrastructural damage to organelles such as the mitochondria. The ideal cardioplegic solution should produce 100% functional recovery with no ventricular arrhythmia, cytosolic calcium overload or other pump abnormalities. There is no cardioplegic solution currently available which fulfils all these requirements. We have now found that the heart can be better protected during arrest and recovery by using the potassium channel opener adenosine and the local anaesthetic lignocaine.

The action of adenosine is controversial. Adenosine has been shown to increase coronary blood flow, hyperpolarise the cell membrane and act as a preconditioning agent via the ATP-sensitive potassium channel and adenosine related pathways including adenosine receptors notably the Al receptor. Adenosine is also known to improve myocardial recovery as an adjunct to high potassium cardioplegia. Furthermore, adenosine can be used as a pretreatment (whether or not it is present in the arresting solution) to reduce lethal injury. In one study, adenosine was shown to rival potassium arrest solutions and more recently in blood cardioplegia, it prevented post-ischaemic dysfunction in ischaemically injured hearts. Adenosine is sometimes added as an adjunct to potassium cardioplegia.

Lignocaine is a local anaesthetic which blocks sodium fast channels and has antiarrhythmatic properties by reducing the magnitude of inward sodium current. The accompanying shortening of the action potential is thought to directly reduce calcium entry into the cell via $Ca^{2+}$ selective channels and $Na^+/Ca^{2+}$ exchange. Recent reports also implicate lignocaine with the scavenging of free radicals such as hydroxyl and singlet oxygen in the heart during reperfusion. Associated with this scavenging function, lignocaine may also inhibit phospholipase activity and minimise membrane degradation during ischaemia. Lignocaine has also been shown to have a myocardial protective effect and in one study was found to be superior to high potassium solutions. However, our experiments show that lignocaine alone at 0.5, 1.0 and 1.5 mM gave highly variable functional recoveries using the isolated working rat heart.

According to one aspect of the present invention there is provided a method for arresting, protecting and/or preserving an organ which includes administering effective amounts of (i) a potassium channel opener or agonist and/or an adenosine receptor agonist and (ii) a local anaesthetic to a subject in need thereof.

According to another aspect of the present invention there is provided the use of (i) a potassium channel opener or agonist and/or an adenosine receptor agonist and (ii) a local anaesthetic in the manufacture of a medicament for arresting, protecting and/or preserving an organ.

The present invention also provides (i) a potassium channel opener or agonist and/or an adenosine receptor agonist and (ii) a local anaesthetic for use in arresting, protecting and/or preserving an organ.

According to a further aspect of the present invention there is provided a pharmaceutical or veterinary composition which includes effective amounts of (i) a potassium channel opener or agonist and/or an adenosine receptor agonist and (ii) a local anaesthetic.

Wile the present invention is particularly advantageous in arresting, protecting and/or preserving an organ while it is intact in the body of the subject, it will be appreciated that it may also be used to arrest, protect and/or preserve isolated organs.

Thus, the present invention still further provides a method for arresting, protecting and/or preserving an organ which includes adding a composition which includes effective amounts of (i) a potassium channel opener or agonist and/or an adenosine receptor agonist and (ii) a local anaesthetic to the organ.

The term "adding" is used herein in its broadest sense to refer to any methods of exposing the organ to the composition of the present invention, for example, bathing, perfusing or pumping via various routes.

The term "organ" is used herein in its broadest sense and refers to any part of the body exercising a specific function including tissues and cells or parts thereof, for example, cell lines or organelle preparations. Other examples include circulatory organs such as the heart, respiratory organs such as the lungs, urinary organs such as the kidneys or bladder, digestive organs such as the stomach, liver, pancreas or spleen, reproductive organs such as the scrotum, testis, ovaries or uterus, neurological organs such as the brain, germ cells such as spermatozoa or ovum and somatic cells such as skin cells, heart cells i.e., myocytes, nerve cells, brain cells or kidney cells.

The method of the present invention is particularly useful in arresting, protecting and/or preserving the heart during open-heart surgery including heart transplants. Other applications include reducing heart damage before, during or following cardiovascular intervention which may include a heart attack, angioplasty or angiography. For example, the composition could be administered to subjects who have suffered or are developing a heart attack and used at the time of administration of blood clot-busting drugs such as streptokinase. As the clot is dissolved, the presence of the composition may protect the heart from further injury such as reperfusion injury. The composition may be particularly effective as a cardioprotectant in those portions of the heart that have been starved of normal flow, nutrients and/or oxygen for different periods of time. For example, the composition may be used to treat heart ischaemia which could be pre-existing or induced by cardiovascular intervention.

Thus, the present invention also provides a cardioplegic or cardioprotectant composition which includes effective amounts of (i) a potassium channel opener or agonist and/or an adenosine receptor agonist and (ii) a local anaesthetic.

The potassium channel openers or agonists may be selected from nicorandil, diazoxide, minoxidil, pinicadil, aprikalim, cromokulim, NS-1619 (1,3-dihydro-1-[2-hydroxy5-(trifluoromethyl)phenyl]5-(trifluoromethyl)2—H-benimidazol-one), amlodipine, Bay K 8644(L-type)(1,4-dihydro-26-dimethyl-5-nitro-4[2(trifluoromethyl)phenyl]-3-pyridine carboxylic acid (methyl ester)), bepridil HCl (L-type), calciseptine (L-type), omega-conotoxin GVIA (N-type), omega-conotoxin MVIIC(Q-type), cyproheptadine HCl, dantrolene sodium ($Ca^{2+}$ release inhibitor), diltiazem HCl (L-type), filodipine, flunarizine HCl ($Ca^{2+}/Na^+$), fluspirilene (L-type), HA-1077 2 HCl(1-(5 isoquinolinyl sulphonyl) homo piperazine HCl), isradipine, loperamide HCl, manoalide ($Ca^{2+}$ release inhibitor), nicardipine HCl (L-type), nifedipine (L-type), niguldipine HCl (L-type), nimodipine (L-type), nitrendipine (L-type), pimozide (L- and T-type), ruthenium red, ryanodine (SR channels), taicatoxin, verapamil HCl (L-type), methoxy-verapamil HCl (L-type), YS-035 HCl (L-type)N[2(3,4-dimethoxyphenyl) ethyl]-3,4-dimethoxy N-methyl benzene ethaneamine HCl) and AV blockers such as verapamil and adenosine. It will be appreciated that this list includes calcium antagonists as potassium channel openers are indirect calcium antagonists.

Adenosine is particularly preferred as it is capable of opening the potassium channel, hyperpolarising the cell, depressing metabolic function, possibly protecting endothelial cells, enhancing preconditioning of tissue and protecting from ischaemia or damage. Adenosine is also an indirect calcium antagonist, vasodilator, antiarrhythmic, antiadrenergic, free radical scavenger, arresting agent, anti-inflammatory agent (attenuates neutrophil activation), metabolic agent and possible nitric oxide donor.

In a preferred embodiment, the present invention provides a method for arresting, protecting and/or preserving an organ which includes administering effective amounts of adenosine and a local anaesthetic to a subject in need thereof.

Suitable adenosine receptor agonists include $N^6$-cyclopentyladenosine (CPA), N-ethylcarboxamido adenosine (NECA), 2-[p-(2-carboxyethyl)phenethyl-amino-5'-N-ethylcarboxamido adenosine (CGS-21680), 2-chloroadenosine, $N^6$-[2-(3,5-dimethoxyphenyl)-2-(2-methoxyphenyl]ethyladenosine, 2-chloro-$N^6$-cyclopentyladenosine (CCPA), N-(4-aminobenzyl)-9-[5-(methylcarbonyl)-beta-D-robofuranosyl]-adenine (AB-MECA), ([IS-[1a,2b,3b,4a(S*)]]-4-[7-[[2-(3-chloro-2-thienyl)-1-methyl-propyl]amino]-3H-imidazole[4,5-b] pyridyl-3-yl]cyclopentane carboxamide (AMP579), $N^6$-(R)-phenylisopropyladenosine (R-PLA), aminophenylethyladenosine 9 APNEA) and cyclohexyladenosine (CHA).

The local anaesthetic can be selected from mexiletine, diphenylhydantoin prilocaine, procaine, mepivacaine and Class 1B antiarrhythmic agents such as lignocaine or derivatives thereof, for example, QX-314. Lignocaine is preferred as it is capable of acting as a local anaesthetic probably by blocking sodium fast channels, depressing metabolic function, lowering free cytosolic calcium, protecting against enzyme release from cells, possibly protecting endothelial cells and protecting against myofilament damage. Lignocaine is also a free radical scavenger and an antiarrhythmic.

As lignocaine acts by blocking sodium fast channels, it will be appreciated that other sodium channel blockers could be used instead of or in combination with the local anaesthetic in the method and composition of the present invention. Examples of suitable sodium channel blockers include venoms such as tetrodotoxin.

Thus, in a particularly preferred embodiment there is provided a method for arresting, protecting and/or preserving an organ which includes administering effective amounts of adenosine and lignocaine to a subject in need thereof.

In another preferred embodiment there is provided a pharmaceutical or veterinary composition which includes effective amounts of adenosine and lignocaine.

For ease of reference, the "potassium channel opener or agonist and/or adenosine receptor agonist" and the "local anaesthetic" will hereinafter be referred to as the "active ingredients".

The method of the present invention involves the administration of effective amounts of the active ingredients for a time and under conditions sufficient for the organ to be arrested, protected and/or preserved. The active ingredients may be administered separately, sequentially or simultaneously and in a single dose or series of doses.

The subject may be a human or an animal such as a livestock animal (e.g. sheep, cow or horse), laboratory test animal (e.g. mouse, rabbit or guinea pig) or a companion animal (e.g. dog or cat), particularly an animal of economic importance.

It will be appreciated that the amounts of active ingredients present in the composition will depend on the nature of the subject, the type of organ being arrested, protected and/or preserved and the proposed application. In the case of a human subject requiring heart arrest during open-heart surgery, the concentration of adenosine is preferably about 0.001 to about 2 mM, more preferably about 0.01 to about 10 mM, most preferably about 0.05 to about 5 mM and the concentration of lignocaine is preferably about 0.001 to about 2 mM, more preferably about 0.01 to about 10 mM, most preferably about 0.05 to about 5 mM. In the case of a human subject requiring treatment before, during or to following a heart attack or cardiovascular intervention, the preferred concentrations of adenosine and lignocaine are set out in the table below.

| Site of Injection | Type/Units | Adenosine | Lignocaine |
|---|---|---|---|
| Intravenous | Infusion mg/min/kg | 1. 0.001–10<br>2. 0.01–5<br>3. 0.01–1 | 1. 0.0001–20<br>2. 0.01–10<br>3. 0.5–3 |
| Intravenous | Bolus mg/kg | 1. 0.0001–100<br>2. 0.001–10<br>3. 0.01–0.5 | 1. 0.001–1000<br>2. 0.01–100<br>3. 0.05–2.5 |
| Intracoronary | Infusion mg/min (per heart) | 1. 0.0001–100<br>2. 0.001–1<br>3. 0.01–0.5 | 1. 005–50<br>2. 0.005–5<br>3. 0.05–2.5 |
| Intracoronary | Bolus µg (per heart) | 1. 0.001–1000<br>2. 0.1–100<br>3. 1–20 | 1. 0.01–10,000<br>2. 1–1000<br>3. 10–200 |

1. = preferably
2. = more preferably
3. = most preferably

The active ingredients may be administered by any suitable route including oral, implant, rectal, inhalation or insufflation (through the mouth or nose), topical (including buccal and sublingual), vaginal and parenteral (including subcutaneous, intramuscular, intravenous, intrasternal and intradermal). Preferably, administration in open-heart surgery or cardiovascular intervention applications will be achieved by mixing the active ingredients with the blood of the subject or subjects having a similar blood type. The active ingredients then enter the coronary circulation generally via the aorta. Arrest may also be achieved by either continuous or intermittent delivery. For example, heart arrest may occur by either continuous or intermittent perfusion retrograde through the aorta in the Langendorff mode. However, it will be appreciated that the preferred route will vary with the condition and age of the subject and the chosen active ingredients.

The composition of the present invention is highly beneficial at about 15° C. to about 37° C., preferably about 20° C. to about 37° C., where longer arrest times using St Thomas No. 2 solution can only be achieved when the temperature is lowered, for example, down to about 4° C.

While it is possible for one or both of the active ingredients to be administered alone, it is preferable to administer one or both of them together with one or more pharmaceutically acceptable carriers, diluents adjuvants and/or excipients. Each carrier, diluent, adjuvant and/or excipient must be pharmaceutically "acceptable" in the sense of being compatible with the other ingredients of the composition and not injurious to the subject. The compositions may conveniently be presented in unit dosage form and may be prepared by methods well known in the art of pharmacy. Such methods include the step of bringing into association the active ingredient with the carrier which constitutes one or more accessory ingredients. Preferably, the compositions are prepared by uniformly and intimately bringing into association the active ingredient with liquid carriers, diluents, adjuvants and/or excipients.

The present invention also extends to a pharmaceutical or veterinary composition which includes the active ingredients and a pharmaceutically or veterinarily acceptable carrier, diluent, adjuvant and/or excipient.

Compositions of the present invention suitable for oral administration may be presented as discrete units such as capsules, sachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredients may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. pregelatinised maize starch, polyvinylpyrrolidone or hydroxypropyl methyl cellulose), fillers (e.g. lactose, microcyrstalline cellulose or calcium hydrogen phosphate), lubricants (e.g. magnesium stearate, talc or silica), inert diluent, preservative, disintegrant (e.g. magnesium stearate, talc or silica), inert diluent, preservative, disintegrant (e.g. sodium starch glycollate, cross-linked povidone, cross-linked sodium carboxymethyl cellulose), surface-active or dispersing agents. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Liquid preparations for administration prior to arresting, protecting and/or preserving the organ may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); preservatives (e.g. methyl or propyl-p-hydroxybenzoates or sorbic acid); and energy sources (e.g. carbohydrates such as glucose, fats such as palmitate or amino acid).

Compositions suitable for topical administration in the mouth include lozenges comprising the active ingredients in a flavoured basis, usually sucrose and acacia or tragacanth gum; pastilles comprising the active ingredients in an inert basis such as gelatin and glycerin, or sucrose and acacia gum; and mouthwashes comprising the active ingredients in a suitable liquid carrier.

For topical application for the skin, the active ingredients may be in the form of a cream, ointment, jelly, solution or suspension.

For topical application to the eye, the active ingredients may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine and thickening agents such as hypromellose may also be included.

The active ingredients may also be formulated as depot preparations. Such long acting formulations may be administered by implantation (e.g. subcutaneously or intramuscularly) or by intramuscular injection. Thus, for example, the active ingredients may be formulated with suitable polymeric or hydrophobic materials (e.g. as an emulsion in an acceptable oil or ion exchange resins, or as sparingly soluble derivatives, for example, as a sparingly soluble salt.

Compositions for rectal administration may be presented as a suppository or retention enema with a suitable non-irritation excipient which is solid at ordinary temperatures but liquid at the rectal temperature and will therefore melt in the rectum to release the active ingredients. Such excipients include cocoa butter or a salicylate.

For intranasal and pulmonary administration, the active ingredients may be formulated as solutions or suspensions for administration via a suitable metered or unit dose device or alternatively as a powder mix with a suitable carrier for administration using a suitable delivery device.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bacteriostats and solutes which render the composition isotonic with the blood of the intended subject; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

When the composition is for veterinary use it may be prepared, for example, by methods that are conventional in the art. Examples of such veterinary compositions include those adapted for (a) oral administration, external application, for example drenches (e.g. aqueous or non-aqueous solutions or suspensions); tablets or boluses; powders, granules or pellets for admixture with foodstuffs; pastes for application to the tongue;

(b) parenteral administration for example by subcutaneous, intramuscular or intravenous injection, e.g. as a sterile solution or suspension; or (when appropriate) by intravenous injection where a suspension or solution is introduced into the udder via the teat;

(c) topical application, e.g. as a cream, ointment or spray applied to the skin; or (d) intravaginally, e.g. as a pessary, cream or foam.

It should be understood that in addition to the ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents.

Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, steric acid, sodium oleate, sodium chloride or talc. Suitable time delay agents include glyceryl monostearate or glyceryl distearate.

A preferred pharmaceutically acceptable carrier is a buffer having a pH of about 6 to about 9, preferably about 7, more preferably about 7.4 and/or low concentrations of potassium, for example, up to about 10 mM, more preferably about 2 to about 8 mM, most preferably about 4 to about 6 mM. Suitable buffers include Krebs-Henseleit which generally contains 10 mM glucose, 117 mM NaCl, 5.9 mM KCl, 25 mM $NaHCO_3$, 1.2 mM $NaH_2PO_4$, 1.12 mMCaCl$_2$ (free $Ca^{2+}$=1.07 mM) and 0.512 mM $MgCl_2$ (free $Mg^{2+}$=0.5 mM), St. Thomas No. 2 solution, Tyrodes solution which generally contains 10 mM glucose, 126 mM NaCl, 5.4 mM KCl, 1 mM $CaCl_2$, 1 mM $MgCl_2$, 0.33 mM $NaH_2PO_4$ and 10 mM HEPES (N-[2-hydroxyethyl]piperazine-N'-[2-ethane sulphonic acid], Fremes solution, Hartmanns solution which generally contains 129 NaCl, 5 mM KCl, 2 mM $CaCl_2$ and 29 mM lactate and Ringers-Lactate. One advantage of using low potassium is that it renders the present composition less injurous to the subject, in particular pediatric subjects such as neonates/infants. High potassium has been linked to an accumulation of calcium which may be associated with irregular heart beats during recovery, heart damage and cell swelling. Neonates/infants are even more susceptible than adults to high potassium damage during cardiac arrest. After surgery for defects a neonate/infant's heart may not return to normal for many days, sometimes requiring intensive therapy or life support. It is also advantageous to use carriers having low concentrations of magnesium, such as, for example up to about 2.5 mM, but it will be appreciated that high concentrations of magnesium, for example up to about 20 mM, can be used if desired without substantially effecting the activity of the composition.

In a further preferred embodiment the present invention provides a pharmaceutical or veterinary composition which includes adenosine, lignocaine and a pharmaceutically acceptable carrier which contains up to about 10 mM potassium.

In a still further preferred embodiment, the present invention provides a pharmaceutical or veterinary composition which includes adenosine, lignocaine and Krebs-Henseleit buffer.

The composition may also advantageously be presented in the form of a kit in which the active ingredients are held separately for separate, sequential or simultaneous administration.

It will be appreciated that the composition of the present invention may also include and/or be used in combination with known medicaments depending on the proposed application. For instance, medicaments which substantially prevent the breakdown of adenosine in the blood such as nucleoside transport inhibitors, for example, dipyridamole could be used as additives in the composition of the present invention. The half life of adenosine in the blood is about 10 seconds so the presence of a medicament to substantially prevent its breakdown will maximise the effect of the composition of the present invention. Dipyridamole could advantageously be included in concentrations from about 0.1 nM to about 10 mM and has major advantages with respect to cardioprotection. Dipyridamole may supplement the actions of adenosine by inhibiting adenosine transport which increases vasodilation. This could be particularly important when the composition is administered intermittently.

Other examples of medicaments include clot-busting drugs such as streptokinase. As discussed earlier, the composition could be administered at the time of administration of streptokinase in subjects who have suffered or are developing a heart attack.

The invention will now be described with reference to the following examples. These examples are not to be construed as limiting in any way.

In the example, reference will be made to the accompanying drawings in which.

Figure 1:
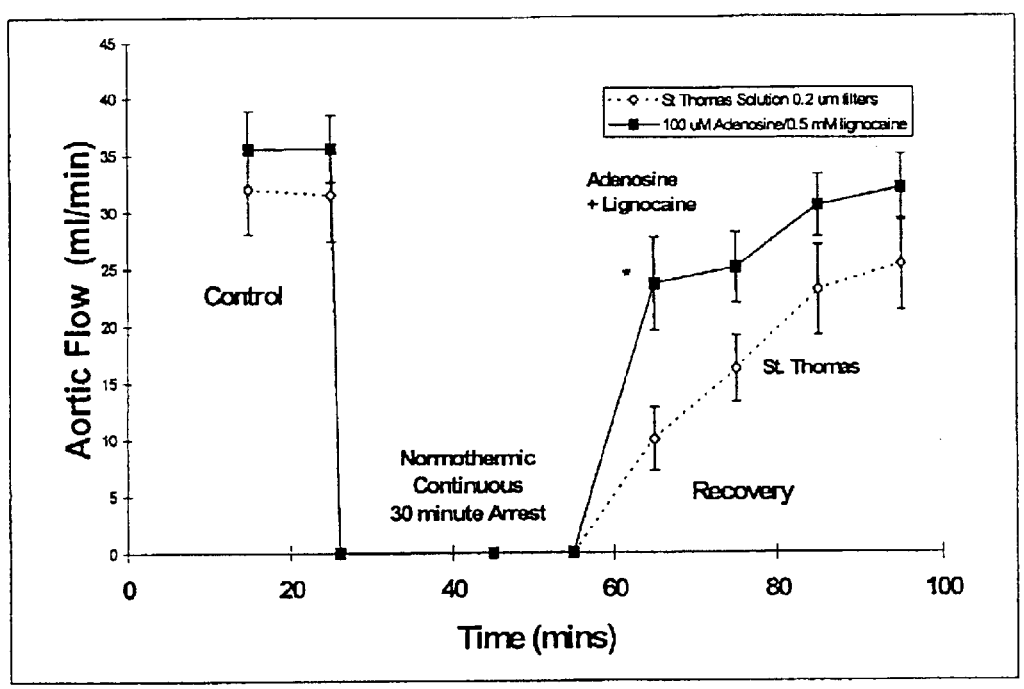
FIG. 1 is a graph of aortic flow vs time comparing hearts arrested using 100 μM adenosine and 0.5 mM lignocaine in Krebs-Henseleit and St. Thomas Hospital No. 2 solution.

In the examples, "AL" refers to compositions containing adenosine and lignocaine.

EXAMPLE 1

This example compares the effects of adenosine (100 μM) cardioplegia with hyperkalemic St. Thomas Hospital No. 2 solution (16 mM $K^+$) on functional recovery after a period of global ischaemia using continuous perfusion.

Hearts from male 450 g Sprague-Dawley rats (n=19) were perfused for 30 minutes in the working mode (preload 7.5 mmHg; afterload 100 mmHg) with Krebs-Henseleit pH 7.4 buffer at 37° C. Hearts were then arrested in a retrograde mode at a constant pressure of 70 mmHg with either (i) a solution containing 100 μM adenosine and 0.5 mM lignocaine in filtered Krebs-Henseleit (10 mM glucose, pH 7.6–7.8 @ 37° C.) (n=11) or (ii) St. Thomas No 2 solution (0,2 micron filter) (n=8). Following either 30 minutes or 4 hrs of arrest, the hearts were switched back to normal antegrade perfusion with Krebs-Henseleit pH 7.4 @ 37° C. Heart rate, coronary flow, aortic flow, aortic pressure and oxygen consumption were monitored. Statistical significance was assessed using a Student t-Test.

Results

Hearts arrested for 30 minutes using adenosine cardioplegia achieved quiescence in half the time compared to St. Thomas No. 2 solution (30 vs 77 seconds, p<0.0001). During arrest under a constant perfusion pressure, coronary blood flow was 30% greater using adenosine cardioplegia (p<0.05). Faster recoveries were found in AL hearts in aortic pressure, aortic flow and cardiac output during reperfusion. After 5 min into reperfusion, the heart rate, aortic pressures, aortic flow, coronary flow, cardiac output and $O_2$ consumption were higher in the AL hearts (Table 1). Higher aortic flows were also found at 15, 25 and 35 min against a perfusion head of 100 mmHg (FIG. 1).

TABLE 1

Comparison between adenosine and lignocaine cardioplegia and St Thomas No 2 Hospital solution after 30 min Normothermic Continuous Arrest in the working rat heart (37° C.)

| | Adenosine and lignocaine (n = 11) | | | Thomas No 2 Solution (n = 12) | | |
|---|---|---|---|---|---|---|
| | Time to electromechanical arrest (sec) | | | | | |
| | 30 ± 2 sec | | | 77 ± 6 sec | | |
| Parameter | Control | 5 min Recovery | % Control | Control | 5 min Recovery | % Control |
| Heart (bpm) | 292 ± 9 | 213 ± 8 | 73% | 285 ± 14 | 150 ± 35 | 53% |
| Systolic pressure (mmHg) | 122 ± 3 | 126 ± 4 | 103% | 126 ± 3 | 88 ± 14 | 70%* |
| Diastolic Pressure (mmHg) | 76 ± 1 | 74 ± 1.3 | 97% | 78.5 ± 1.2 | 59 ± 8.5 | 75% |
| Aortic flow (ml/min) | 35.6 ± 3 | 24 ± 4 | 67% | 31.5 ± 4.1 | 9.96 ± 2.8 | 32%* |
| Coronary flow (ml/min) | 16.4 ± 0.7 | 13.6 ± 0.9 | 83% | 17.4 ± 0.74 | 10 ± 1.9 | 57% |
| Cardiac Output (ml/min) | 52 ± 3 | 37.2 ± 4.7 | 72% | 50 ± 4 | 20 ± 4.5 | 40%* |
| $O_2$ consumption (μmol/min/g wet wt) | 6.97 ± 0.28 | 5.39 ± 0.38 | 77% | 7.28 ± 0.30 | 4.14 ± 0.5 | 57% |

Control values are taken 5 min prior to the 30 min arrest protocol.
*Significant P < 0.05

In terms of functional parameters, 100 μM adenosine and 0.5 mM lignocaine cardioplegia lead to shorter arrest times and an enhanced recovery profile compared to the St. Thomas Hospital No. 2 solution.

The results for hearts arrest for 4 hrs are shown in Table 2 below.

TABLE 2

Comparison of functional Recovery of S-D Rat Hearts After 30 min Continuous Cardioplegia With Adenosine/Lignocaine Cardioplegia or St Thomas Hospital Solution No. 2

| | n | Heart Rate (bpm) | Systolic Pressure (mmHg) | Coronary Flow (ml/min) | Aortic Flow (ml/min) | Cardiac Output (ml/min) | MV02 (μmol/min/g) | Arrest |
|---|---|---|---|---|---|---|---|---|
| Stable Perfusion Period | | | | | | | | |
| Adenosine + Lignocaine Cardioplegia | 7 % | 292.18 ± 8.82 100 | 122.38 ± 3.58 100 | 16.44 ± 1.07 100 | 35.66 ± 3.33 100 | 52 ± 2.73 100 | 6.97 ± 0.28 100 | 30 min Cardioplegic Arrest with Constant Perfusion Delivered |

TABLE 2-continued

Comparison of functional Recovery of S-D Rat Hearts After 30 min Continuous Cardioplegia
With Adenosine/Lignocaine Cardioplegia or St Thomas Hospital Solution No. 2

|  | n | Heart Rate (bpm) | Systolic Pressure (mmHg) | Coronary Flow (ml/min) | Aortic Flow (ml/min) | Cardiac Output (ml/min) | MV02 ($\mu$mol/min/g) | Arrest |
|---|---|---|---|---|---|---|---|---|
| St Thomas Hospital Solution No 2 | 10 % | 2.85 ± 13.48 100 | 128.08 ± 3.14 100 | 17.4 ± 0.74 100 | 31.53 ± 4.09 100 | 48.93 ± 4.15 100 | 7.28 ± 0.3 100 | at 70 mmHg |
| After 5 min Reperfusion | | | | | | | | |
| Adenosine + Lignocaine Cardioplegia | 7 % | 212.91 ± 7.62 73 | 126.09 ± 4.15 103 | 13.6 ± 0.92 83 | 23.64 ± 4.09 66 | 37.24 ± 4.73 72 | 5.39 ± 0.38 77 | |
| St Thomas Hospital Solution No. 2 | 10 % | 150.36 ± 34.45 53 | 88.08 ± 14.21 70 | 10.09 ± 1.93 57 | 9.96 ± 2.83 32 | 20.06 ± 4.49 40 | 4.14 ± 0.5 57 | |
| After 15 min Reperfusion | | | | | | | | |
| Adenosine + Lignocaine Cardioplegia | 7 % | 262.18 ± 10.36 90 | 114.91 ± 4.18 94 | 12.55 ± 1.03 76 | 25.07 ± 3.08 71 | 37.82 ± 3.89 72 | 5.89 ± 0.32 86 | |
| St Thomas Hospital Solution No. 2 | 10 % | 257.09 ± 14.81 90 | 118.82 ± 3.81 94 | 15.05 ± 1.24 86 | 16.18 ± 2.95 51 | 31.24 ± 3.73 64 | 6.1 ± 0.45 84 | |
| After 25 min Reperfusion | | | | | | | | |
| Adenosine + Lignocaine Cardioplegia | 7 % | 253.54 ± 28.47 87 | 118.4 ± 3.58 97 | 14.08 ± 0.75 86 | 30.52 ± 2.73 86 | 44.8 ± 3 86 | 8.06 ± 0.31 87 | |
| St Thomas Hospital Solution No. 2 | 10 % | 266.91 ± 15.16 94 | 118.09 ± 3.43 94 | 15.05 ± 1.04 86 | 23.11 ± 3.94 73 | 38.16 ± 4.47 78 | 6.6 ± 0.48 91 | |
| After 35 min Reperfusion | | | | | | | | |
| Adenosine + Lignocaine Cardioplegia | 7 % | 283.83 ± 11.74 97 | 118.88 ± 4.62 97 | 14.2 ± 0.68 88 | 32.13 ± 2.94 90 | 46.33 ± 3.43 89 | 6.54 ± 0.09 94 | |
| St Thomas Hospital Solution No. 2 | 10 % | 271.27 ± 14.04 96 | 120.45 ± 3.11 96 | 15.38 ± 1.37 88 | 25.35 ± 4.03 80 | 40.74 ± 4.4 89 | 6.74 ± 0.48 96 | |

EXAMPLE 2

Adult Wistar rats (350 g) were prepared using the method described in Example 2 and then subjected to intermittent perfusion as discussed below.

Intermittent retrograde perfusion was performed under a constant pressure head of 70 mmHg after hearts were switched back from the working mode to the Lagendorff mode. After stabilisation, the hearts were arrested using 50 ml of either adenosine plus lignocaine cardioplegia or St Thomas Hospital No 2 solution. The aorta was then cross clamped and the heart left to sit arrested for 20 min (except in 30 min intermittent arrest protocol), after which the clamp was released and 2 min of arrest solution delivered from a pressure head of 70 mmHg. The clamp was replaced and this procedure continued for up to 30 mins, 2 hrs and 4 hrs at 37° C.

Intermittent cardioplegic delivery is the method commonly used clinically in contrast to continuous perfusion in Example 1. During Intermittent arrest, the aorta of the subject is clamped and the arrest solution administered. After a few minutes, the heart is arrested and cardioplegia delivery stopped. The heart remains motionless to permit surgery. The arrest solution is administered again every 30 min for few minutes to maintain the heart in the arrested state to preserve and protect the heart muscle. Between these times, the heart muscle slowly becomes ischaemic indicated by the production of lactate and fall in muscle pH. For this reason, intermittent perfusion delivery is often called intermittent ischaemic arrest. The results are shown in Tables 3 to 7 below and FIGS. 2 to 5.

30 min Ischaemic Arrest at 37° C.

Figure 2:
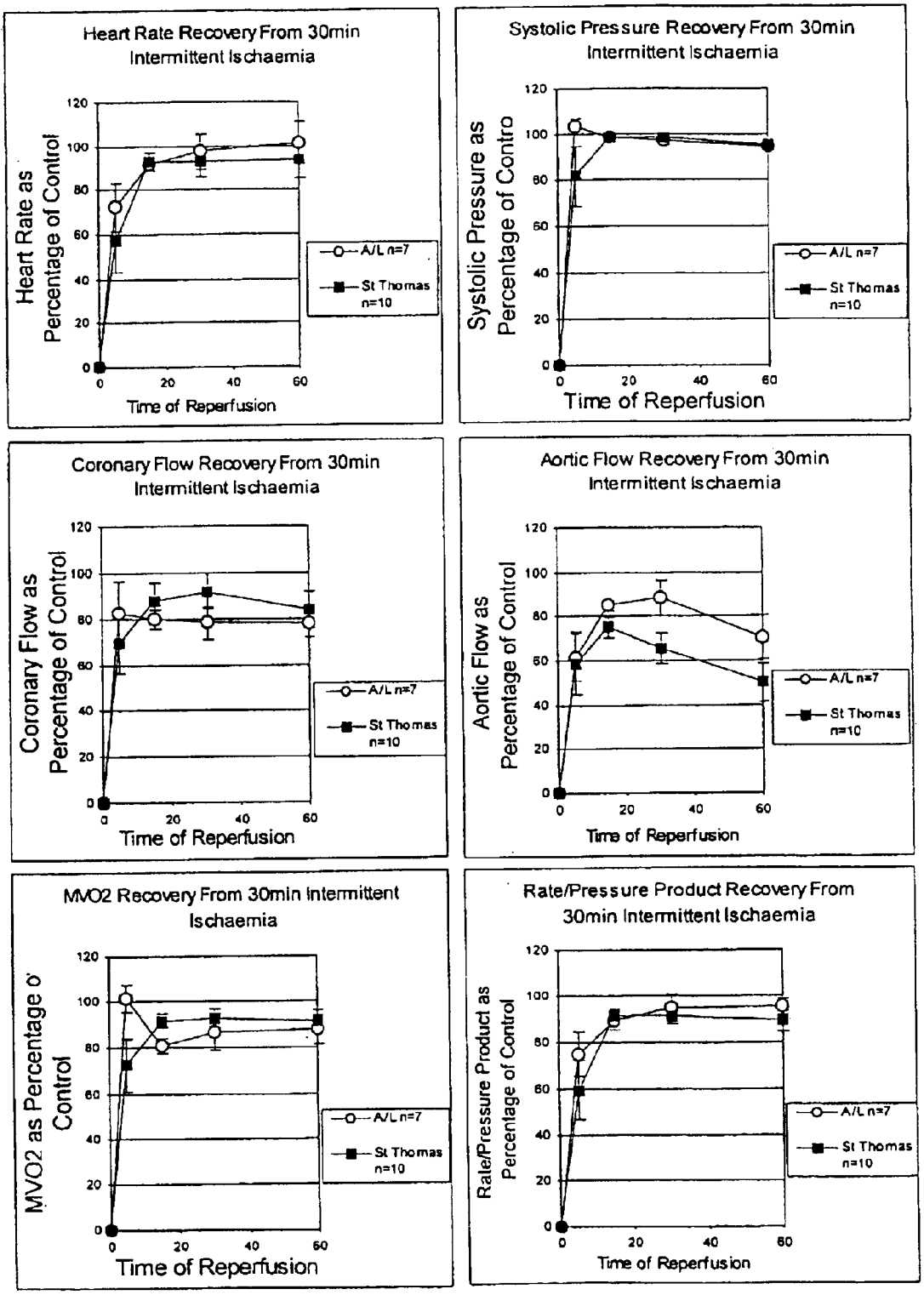
FIG. 2 is six graphs showing heart, rate systolic pressure, aortic flow, coronary flow, MV02 and rate pressure product recovery from 30 mins intermittent ischaemia.

Table 3 and FIG. 2 show that A-L arrests in half the time of St Thomas solution 21s (n=7) vs 53s (n=10). All hearts returned function to the same level following reperfusion (no significant difference between groups).

TABLE 3

Characteristics of Adult Heart 30 min Intermittent Arrest* Achieved by
Adenosine/Lignocaine Cardioplegia and
St Thomas Hospital Solution No. 2
*(2 min cardioplegia pulse after 15 min periods of aortic clamping)

|  | Adenosine/ Lignocaine Cardioplegia (n = 7) | St Thomas Hospital Solution No. 2 (n = 10) | P |
|---|---|---|---|
| Arrest Time (s) | 21.43 ± 3.92 | 52.78 ± 5.65 | p < 0.01 |
| Time to First Contraction Following Reperfusion (s) | 147.14 ± 14.95 | 133.67 ± 31.44 | ns |
| Time to Recover 100 mmHg | 302.14 ± 21.87 | 309.44 ± 30.15 | ns |

TABLE 4

Comparison of functional Recovery of Rat Hearts after 30 min Intermittent Ischaemia*
With Adenosine/Lignocaine Cardioplegia or St Thomas Hospital Solution No 2

|  | n | Heart Rate (bpm) | Systolic Pressure (mmHg) | Aortic Flow (ml/min) | Coronary Flow (ml/min) | Cardiac Output (ml/min) | RP Product (mmHg/min) | MVO2 (μmol/min/g) | Arrest |
|---|---|---|---|---|---|---|---|---|---|
| Stable Perfusion Period | | | | | | | | | |
| Adenosine + Lignocaine Cardioplegia | 7 | 245.38 ± 11.01 | 128.23 ± 2.83 | 34.33 ± 3.64 | 21.64 ± 2.02 | 58.29 ± 4.63 | 31504 ± 1651 | 6.31 ± 0.65 | 30 min Ischaemia Arrest with Cardioplegia Delivered at 15 min |
| St Thomas Hospital Solution No 2 | 10 | 276.74 ± 11.87 100 | 123.64 ± 1.30 100 | 32.78 ± 2.09 100 | 19.38 ± 1.62 100 | 55.36 ± 2.59 100 | 34090 ± 1111 100 | 5.97 ± 0.56 100 | |
| After 5 min Reperfusion | | | | | | | | | |
| Adenosine + Lignocaine Cardioplegia | 7 | 180.48 ± 26.83 74 | 132.79 ± 6.65 104 | 22.06 ± 4.48 64 | *22.15 ± 2.20 102 | 47.59 ± 2.70 82 | 24074 ± 3330 76 | 6.81 ± 0.97 108 | |
| St Thomas Hospital Solution No 2 | 10 | 135.94 ± 32.71 49 | 81.82 ± 15.94 | 19.04 ± 4.69 58 | *13.48 ± 2.47 70 | 34.61 ± 6.96 63 | 23281 ± 4069 68 | 5.02 ± 0.79 84 | |
| After 15 min Reperfusion | | | | | | | | | |
| Adenosine + Lignocaine Cardioplegia | 7 | 225.31 ± 19.17 92 | 126.17 ± 2.88 98 | 29.21 ± 3.20 85 | 17.14 ± 1.81 79 | 48.99 ± 3.76 84 | 28228 ± 2015 90 | 5.03 ± 0.49 80 | |
| St Thomas Hospital Solution No 2 | 10 | 255.88 ± 9.69 92 | 121.56 ± 1.32 98 | 24.84 ± 2.36 76 | 17.00 ± 1.64 88 | 45.07 ± 2.47 81 | 31131 ± 1267 91 | 5.41 ± 0.53 91 | |
| After 30 min Reperfusion | | | | | | | | | |
| Adenosine + Lignocaine Cardioplegia | 7 | 236.94 ± 13.75 97 | 124.84 ± 2.61 97 | 29.60 ± 2.83 86 | 16.49 ± 1.51 76 | 49.09 ± 1.95 84 | 29403 ± 1231 93 | 5.42 ± 0.70 86 | |
| St Thomas Hospital Solution No 2 | 10 | 255.17 ± 12.29 92 | 122.16 ± 1.62 99 | 22.26 ± 3.32 68 | 17.08 ± 1.20 88 | 42.41 ± 3.28 77 | 31154 ± 1464 91 | 5.26 ± 0.38 88 | |
| After 60 min Reperfusion | | | | | | | | | |
| Adenosine + Lignocaine Cardioplegia | 7 | 244.97 ± 11.48 100 | 119.80 ± 2.95 93 | 22.42 ± 3.48 65 | 15.52 ± 0.49 72 | 41.53 ± 2.78 71 | 29269 ± 1240 93 | 5.25 ± 0.55 83 | |
| St Thomas Hospital Solution No 2 | 10 | 258.16 ± 13.88 93 | 117.57 ± 1.68 95 | 17.01 ± 3.08 52 | 15.46 ± 1.21 80 | 35.89 ± 3.46 65 | 30392 ± 1727 89 | 5.08 ± 0.33 85 | |

*Statistically Significant Difference Using Students TTEST (p < 0.05)

2 hr Ischaemic Arrest at 37° C.

Figure 3:
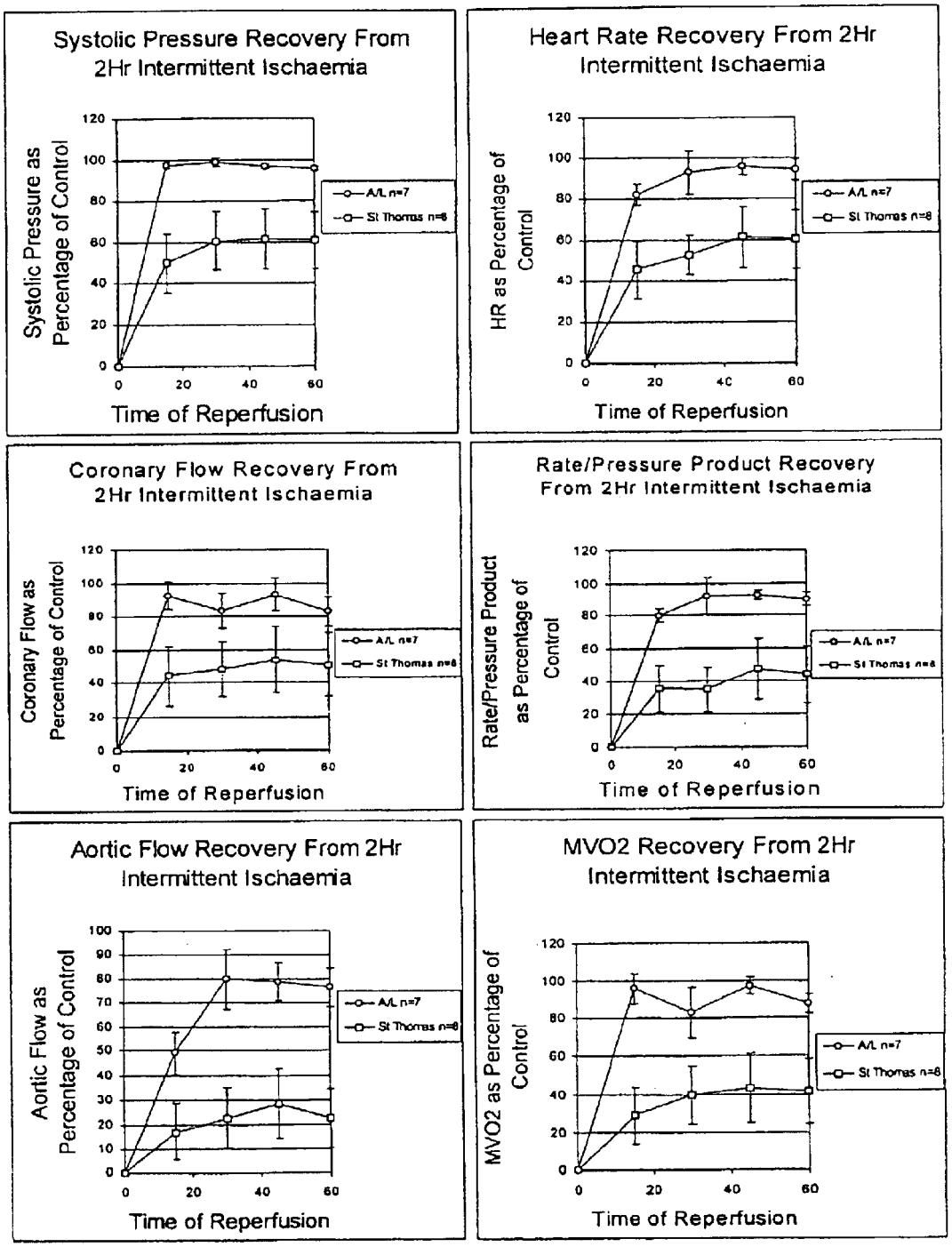
FIG. 3 is six graphs showing heart rate, systolic pressure, aortic flow, coronary flow, MV02 and rate pressure product recovery from 2 hrs intermittent ischaemia.

Table 5 and FIG. 3 show that A-L arrests in half the time of St Thomas solution 33s (n=7) vs 81s (n=8). 4 out of 8 hears arrested with St Thomas did not recover. All A-L hearts survived (n=7). St Thomas hearts which recovered (n=4) had 50–90% aortic flow, 70–120% heart rate and 90–100% systolic pressure. A-L hearts recovered 80% aortic flow, 95% heart rate and 95–100% systolic pressure.

TABLE 5

Characteristics of Adult Rat Heart 2 hr Ischaemic Arrest* Achieved by
Adenosine/Lignocaine Cardioplegia and
St Thomas Hospital Solution No. 2
*(2 min Cardioplegia pulse repeated after 20 min of aortic clamping)

|  | n | Adenosine/ Lignocaine Cardioplegia | n | St Thomas Hospital Solution No. 2 | p |
|---|---|---|---|---|---|
| Arrest Time(s) | 7 | 33 ± 5 | 8 | 81 ± 8 | 0.0003 |
| Time to First Contraction following Reperfusion(s) | 7 | 360 ± 19 | 4 | 260 ± 95 | NS |
| Time to Recover 100 mmHg and Achieve Aortic flow(s) | 7 | 541 ± 46 | 4 | 2400 ± 3261 | NS |
| Percentage of Hearts to Survive Reperfusion | | 100 | | 50 | |

4 hr Ischaemic Arrest at 37° C.

Figure 4:
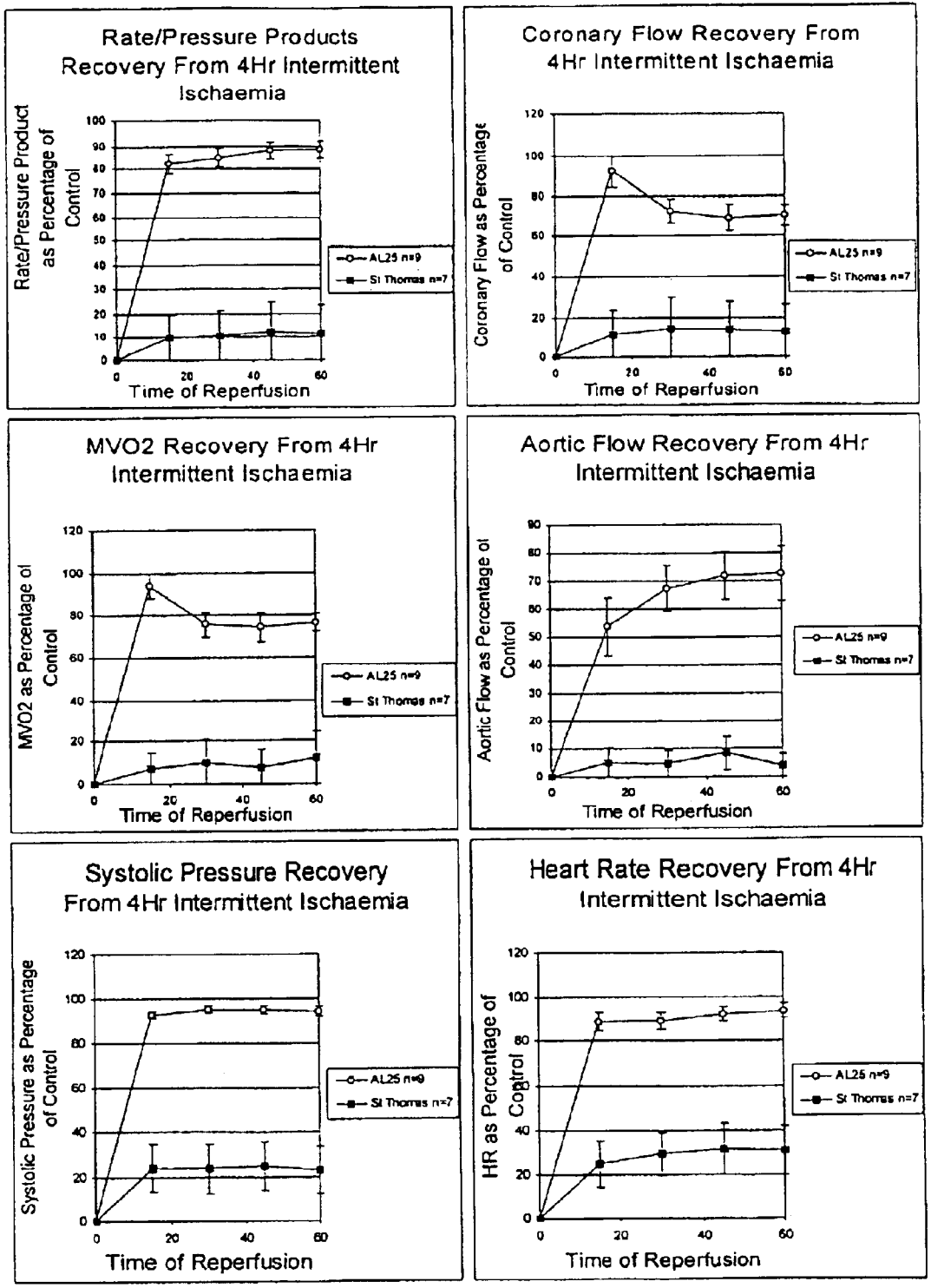
FIG. 4 is six graphs showing heart rate, systolic pressure, aortic flow, coronary flow, MV02 and rate pressure product recovery from 4 hrs intermittent ischaemia.

Tables 6 and 7 and FIG. 4 show A-L arrests in half the time of St Thomas solution (26s (n=9) vs 78s (n=7)). 6 out of 7 hearts arrested with St Thomas did not recover. All A-L hearts survived (n=9). The single St Thomas heart which recovered had 40% aortic flow, 80% heart rate and 90% systolic pressure. A-L hearts recovered 70% aortic flow, 90% heart rate and 95–100% systolic pressure.

TABLE 6

Characteristics of Adult Rat Heart 4 hr Ishaemic Arrest* Achieved by
Adenosine/Lignocaine Cardioplegia and
St Thomas Hospital Solution No. 2
*(2 min cardiplegia pulse repeated after 20 min of aortic clamping)

|  | Adenosine/ Lignocaine Cardioplegia | St Thomas Hospital Solution No. 2 | p |
|---|---|---|---|
| Arrest Time(s) | 26.44 ± 2.77 (n = 9) | 77.86 ± 10 (n = 7) | <0.001 |
| Time to First Contraction following Reperfusion(s) | 401.67 28.48 (n = 9) | 390.00 (n = 1) |  |
| Time to Recover 100 mmHg and Achieve Aortic flow(s) | 549.22 40.68 (n = 9) | 480.00 (n = 1) |  |
| Percentage of Hearts to Survive Reperfusion | 100 (n = 9) | 14 (n = 1) | <0.0001 |

FIGS. 2 to 4 show the functional properties (heart rate, systolic pressure, aortic flow, coronary flow, oxygen consumption and rate-pressure product) during 60 min after 0.5 hr arrest (FIG. 2) 2 hr arrest (FIG. 3) and 4 hrs arrest (FIG. 4). In all cases, hearts arrested with AL solution had higher functional recovery parameters. After 0.5 hr arrest, these differences were not significant except for aortic flow recover in hearts receiving AL arrest solution. Aortic flow against a pressure head of 70 mmHg recovered to 90% of control values at 30 min compared to 65% in St Thomas hearts. After 2 hr intermittent ischaemic arrest the differences in functional recover are more striking. In AL arrested hearts, heart rate and systolic pressure recovered to nearly 100% of control values whereas St. Thomas hearts only recovered 40–50%. Aortic flow, coronary flow, oxygen consumption and rate-pressure product recovered 80% and above the controls in AL hearts and only 20–40% in St Thomas hearts. After 4 hr arrest the differences were even grater with only 1 out of 7 St Thomas hearts recovering. All AL hearts recovered after 4 hr arrest with similar recovery functional profiles described above for 2 hr. It can be

TABLE 7

Comparison of function Recover of Rat Hearts After 4 hr Intermittent Ischaemic Arrest
with Adenosine/Lignocaine Cardioplegia or St Thomas Hospital Solution No. 2

|  | n | Heart Rate (bpm) | Systolic Pressure (mmHg) | Aortic Flow (ml/min) | Coronary Flow (ml/min) | Cardiac Output (ml/min) | RP Product (mmHg/min) | MV02 ($\mu$mol/min/g) | Arrest |
|---|---|---|---|---|---|---|---|---|---|
| Stable Perfusion Period |  |  |  |  |  |  |  |  |  |
| Adenosine + Lignocaine Cardioplegia | 9 | 275.33 ± 12.91 | 118.44 ± 3.50 | 36.47 ± 1.65 | 16.28 ± 1.03 | 53.88 ± 1.73 | 32338 ± 1084 | 6.71 ± 0.45 | 4 hr Ischaemic Arrest with 2 min Cardioplegia Delivered Every 20 min |
| St Thomas Hospital Solution No. 2 | 7 (n = 1) | 259.21 ± 12.84 270 | 121.57 ± 2.42 117.00 | 41.23 ± 4.18 51 | 16.03 ± 1.26 19.8 | 57.26 ± 5.30 70.8 | 31508 ± 1672 315900 | 7.64 ± 0.24 7.28 |  |
| After 15 min Reperfusion |  |  |  |  |  |  |  |  |  |
| Adenosine + Lignocaine Cardioplegia | 9 % | 229.89 ± 16.10 83 | 110.89 ± 1.86 94 | 19.81 ± 3.56 54 | 13.92 ± 1.53 86 | 36.49 ± 4.13 68 | 25327 ± 1555 78 | 5.94 ± 0.69 89 |  |
| St Thomas Hospital Solution No. 2 | 1 % | 220.00 81 | 100 85 | 18.60 36 | 16.20 82 | 36.40 51 | 22000 70 | 5.303 73 |  |
| After 30 min Reperfusion |  |  |  |  |  |  |  |  |  |
| Adenosine + Lignocaine Cardioplegia | 9 % | 239.444 ± 18.7165 87 | 113.00 ± 3.07 95 | 24.62 ± 2.917 68 | 11.53 ± 1.001 71 | 39.44 ± 4.259 73 | 26684 ± 1669 83 | 4.946 ± 0.443 74 |  |
| St Thomas Hospital Solution No. 2 | 1 % | 220 81 | 105.00 90 | 16.8 33 | 20.4 103 | 39.2 55 | 23100 73 | 5.303 73 |  |
| After 60 min Reperfusion |  |  |  |  |  |  |  |  |  |
| Adenosine + Lignocaine Cardioplegia | 9 % | 249.22 ± 17.19 91 | 111.89 ± 3.29 94 | 25.58 ± 3.26 70 | 11.39 ± 1.32 70 | 40.63 ± 4.72 75 | 27570 ± 1577 85 | 5.04 ± 0.49 75 |  |
| St Thomas Hospital Solution No. 2 | 1 % | 250.00 93 | 102.00 87 | 14.40 23 | 18.00 91 | 34.40 49 | 25500 81 | 6.29 86 |  |

Figure 5:
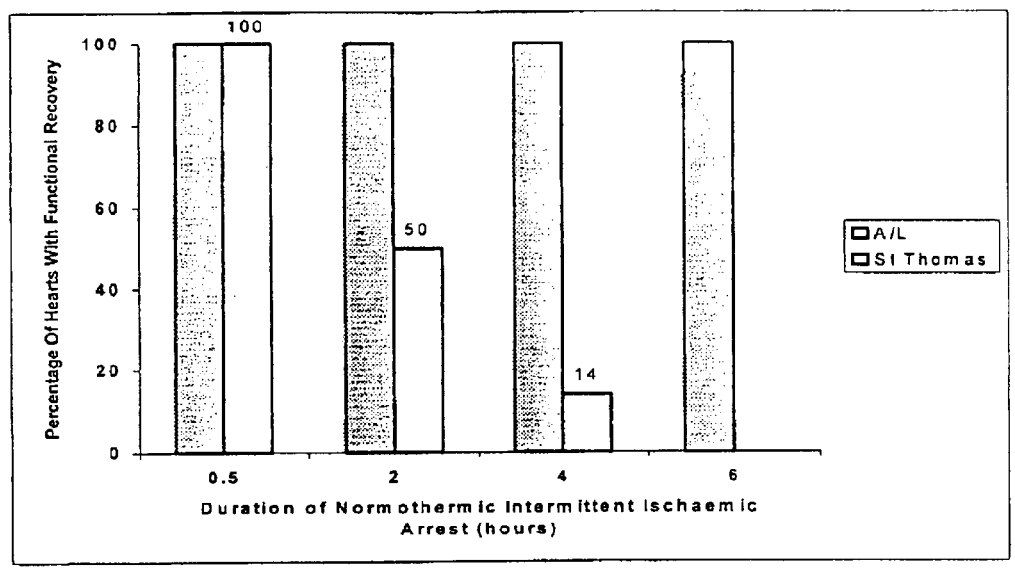
FIG. 5 is a bar graph providing a summary of the results of FIGS. 2 to 4.

FIG. 5 is a summary of the results of FIGS. 2 to 4 which shows hearts arrested with AL solution all survived after 30 min ischaemic intermittent arrest (n=7), 2 hrs intermittent arrest (n=7) and 4 hrs of intermittent arrest (n=9). In contrast, while all hearts arrested with St Thomas solution survived after 30 min (n=10), only 50% (4 out of 8 tested) and 14% survived (1 out of 7) tested. In addition, two hearts have been arrested with AL successfully for 6 hrs (FIG. 5).

concluded that AL arrest provides superior protection during 2 and 4 hr arrest and recovery in adult hearts.

EXAMPLE 3

Neonatal/infant rat hearts (using 50–70 g 20 day old rats) were prepared using the intermittent perfusion technique for 2 hr at 37° C. described in Example 2 except the pressure head of delivery and afterload was reduced to 50 mmHg.

Figure 6:
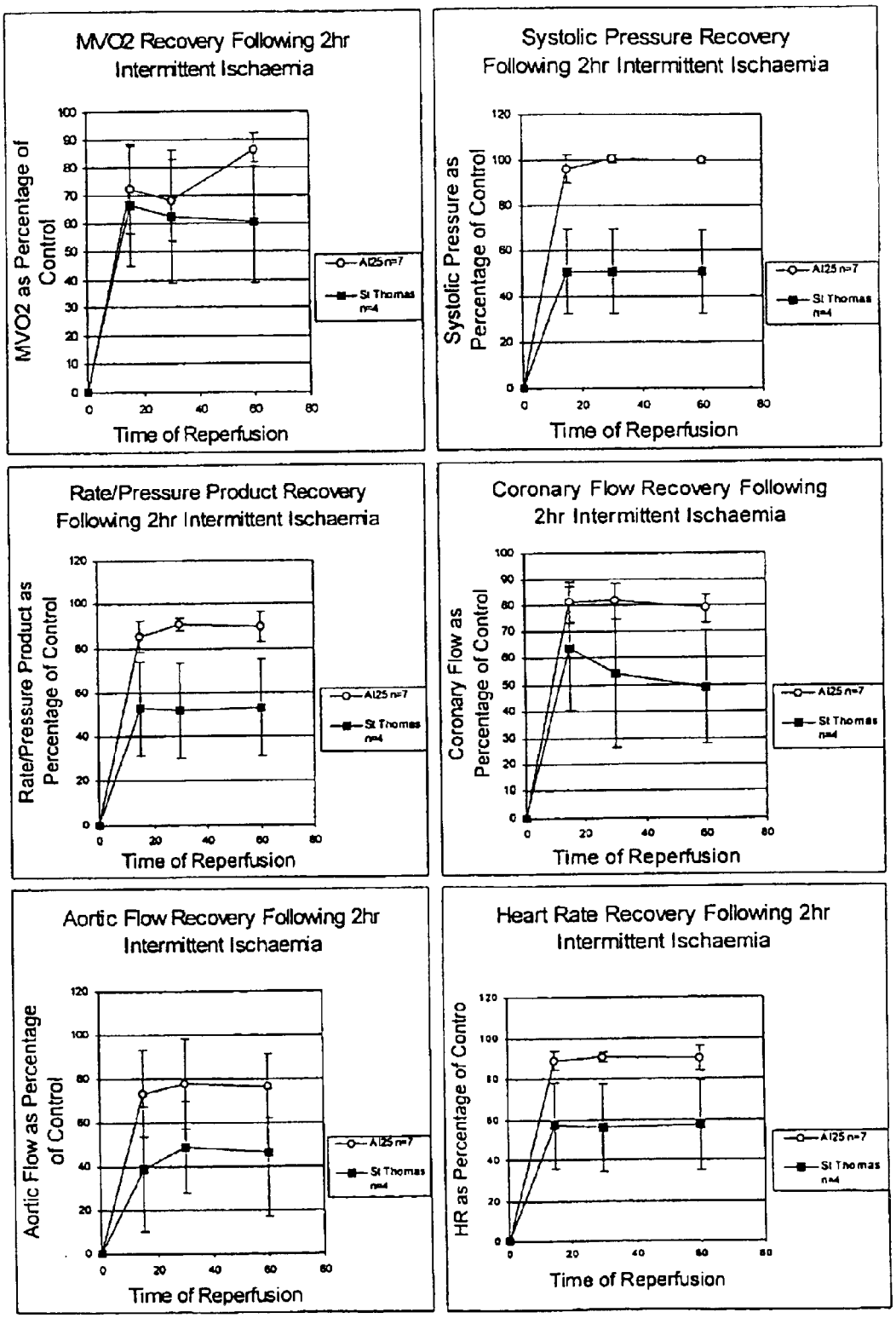
FIG. 6 is six graphs showing heart rate, systolic pressure, aortic flow, coronary flow, MV02 and rate pressure product recovery from 2 hrs of intermittent ischaemia using neonate rat hearts.

The results shown in Tables 8 and 9 below and FIG. 6 show that A-L arrests in a third of the time of St Thomas solution 19s (n=7) vs 66s (n=7). 3 out of 7 hearts arrest with St Thomas did not recover. All A-L hearts survived (n=7) with 80% aortic flow. The St Thomas hearts which recovered averaged 80% aortic flow rate, but this was extremely variable.

All neonatal/infant hearts arrested with AL solution recovered after 2 hr intermittent ischaemic arrest. Only 4 out o 7 hearts arrested with St Thomas solution recovered after 2 hr intermittent ischaemic arrest. In AL arrested hearts, heart rate and systolic pressure recovered to 90–100% of control values wherein St Thomas' hearts there was only 50–60% recovery. Aortic flow, coronary flow and rate-pressure product recovered to 80% and above the controls in AL hearts and only about 50% in St Thomas hearts. Oxygen consumption in the AL hearts was 70–85% of controls and about 60% for the hearts arrested with St Thomas solution. It can be concluded that AL arrest provides superior protection during 2 hr arrest and recover in neonatal/infant hearts.

TABLE 8

Characteristics of Neonatal Immature Rat Heart Arrest* Achieved by Adenosine/Lignocaine Cardioplegia and St Thomas Hospital No. 2
*(2 min Cardioplegia pulse repeated after 20 min of aortic clamping). Reperfusion afterload of 50 mmHg.

|  | Adenosine/ Lignocaine | St Thomas Hospital Solution No. 2 | p |
|---|---|---|---|
| Arrest Time(s) | 18.57 ± 3.72(7) | 65.71* ± 12.71(7) | <0.05 |
| Time to First Contraction Following Reperfusion(s) | 23.83 ± 3.03(7) | 55.75* ± 12.97(4) | <0.05 |
| Time to Recover 50 mmHg Aortic flow(s) | 165 ± 29.48(7) | 270 ± 83.5(4) | ns |
| Percentage of Hearts to Survive Reperfusion | 100(7) | 57*(4) | <0.05 |
| Arrhythmia Occurrence (%) | 14(7) | 25(4) | ns |

*Denotes Statistical Significance $p < 0.05$ using Students t-test

TABLE 9

Comparison of functional Recovery of Immature Rat Hearts After 2 hr Ischemic* Arrest With Adenosine/Lignocaine Cardioplegia or St Thomas Hospital Solution No. 2
*(2 min cardioplegia doses delivered between 20 min periods of aortic clamping)

|  | n | Heart Rate (bpm) | Aortic Flow (ml/min) | Coronary Flow (ml/min) | Cardiac Output (ml/min) | RP Product (mmHg/min) | MV02 (μmol/min/g) | Arrest |
|---|---|---|---|---|---|---|---|---|
| Stable Perfusion Period | | | | | | | | |
| Adenosine + Lignocaine Cardioplegia | 7 | 261.98 ± 12.81 | 6.99 ± 1.30 | 4.80 ± 0.56 | 13.45* ± 1.16 | 16579 ± 853 | 4.60 ± 0.52 | 2 Hr Ischaemic Arrest with 2 min Cardioplegia Delivered Every 20 min |
| St Thomas Hospital Solution No 2 | 7 | 239.96 ± 19.52 | 4.43 ± 1.05 | 4.29 ± 0.76 | 9.95* ± 1.01 | 15515 ± 1149 | 5.39 ± 0.61 | |
| After 15 min Reperfusion | | | | | | | | |
| Adenosine + Lignocaine Cardioplegia | 7 | 230.94 ± 12.33 | 5.37 ± 1.63 | 4.03 ± 0.61 | 11.77 ± 1.84 | 14046 ± 1297 | 4.71 ± 0.33 | |
| St Thomas Hospital Solution No. 2 | 4 | 233.45 ± 36.2 | 3.78 ± 1.51 | 4.58 ± 1.2 | 10.87 ± 1.99 | 13818 ± 3103 | 4.36 ± 0.67 | |
| After 30 min Reperfusion | | | | | | | | |
| Adenosine + Lignocaine Cardioplegia | 7 | 235.39 ± 8.99 | 6.67 ± 1.58 | 4.09 ± 0.68 | 12.45 ± 1.71 | 14994 ± 709 | 4.43 ± 0.24 | |
| St Thomas Hospital Solution No. 2 | 4 | 228.55 ± 32.67 | 4.38 ± 1.68 | 4.00 ± 1.14 | 10.63 ± 1.97 | 13522 ± 2912 | 4.14 ± 0.69 | |
| After 60 min Reperfusion | | | | | | | | |
| Adenosine + Lignocaine Cardioplegia | 7 | 242.78 ± 30.35 | 6 ± 1.66 | 3.75 ± 0.57 | 13.05 ± 1.55 | 13272 ± 2643 | 4.13 ± 0.62 | |
| St Thomas Hospital Solution No 2 | 4 | 234.48 ± 40.16 | 3.88 ± 1.41 | 3.58 ± 0.92 | 9.68 ± 1.50 | 13910 ± 3262 | 4.02 ± 0.75 | |

EXAMPLE 4

Table 10 below shows that adenosine and lignocaine are effective in 1–2 day old neonatal pig heart cardioplegia. (2 hours of 2 min pulses of cardioplegia administered between 20 min periods of aortic clamping).

TABLE 10

| n | Arrest Time (s) | Heart Rate Recovery (After 2 hr Arrest*) |
|---|---|---|
| 1 | 8 | 75% |

EXAMPLE 5

Figure 7:
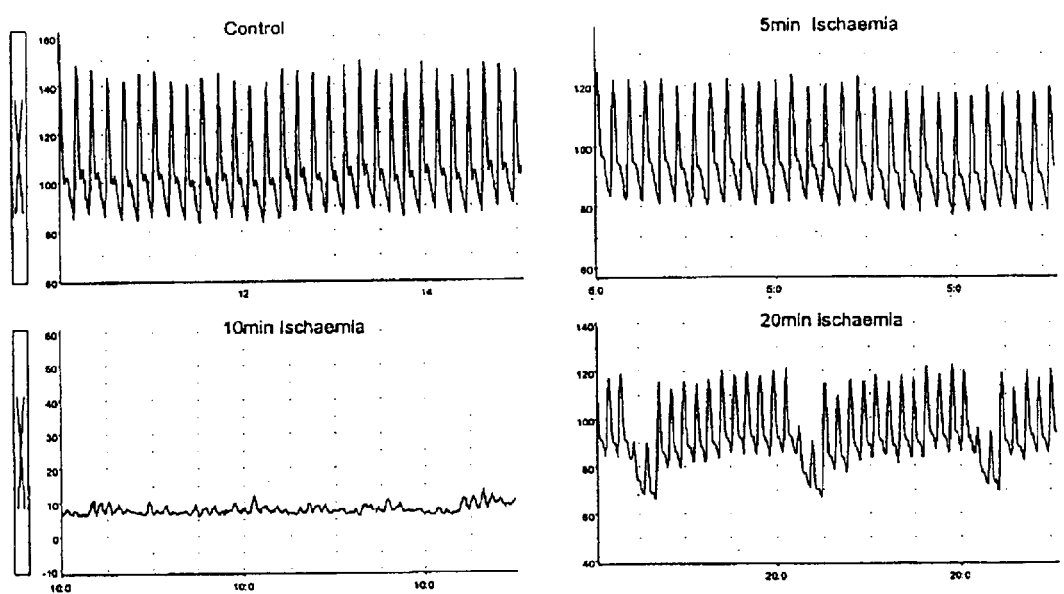
FIG. 7 is four graphs showing 20 min ischaemia in rat heart in vivo following coronary artery ligation with no adenosine-lignocaine infusion.
Figure 8:
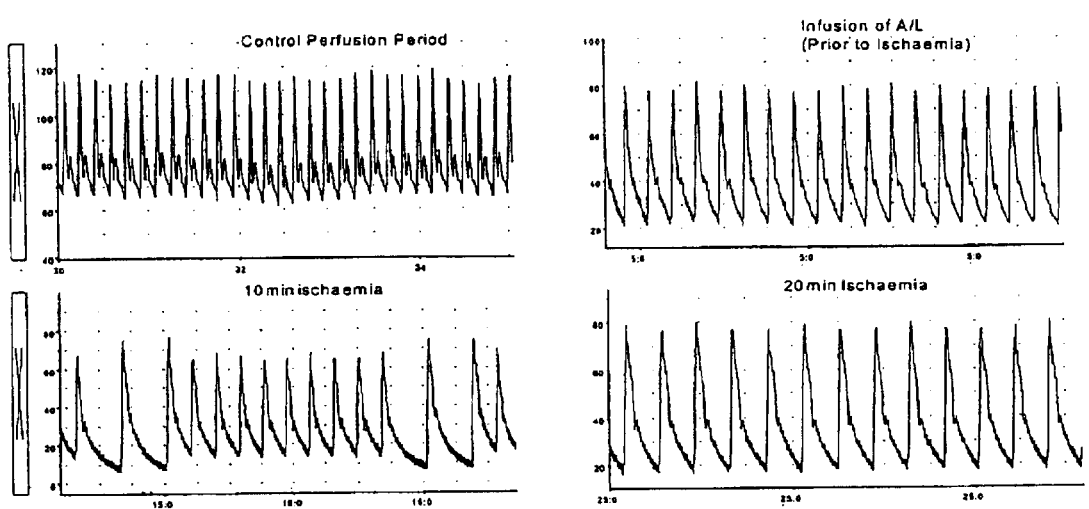
FIG. 8 is four graphs showing 20 min ischaemia in rat heart in Vivo following coronary artery ligation when infused with adenosine (6.3 mg/ml) and lignocaine (12.6 mg/ml) at 1 ml/hour/300 g rat.
Figure 9:
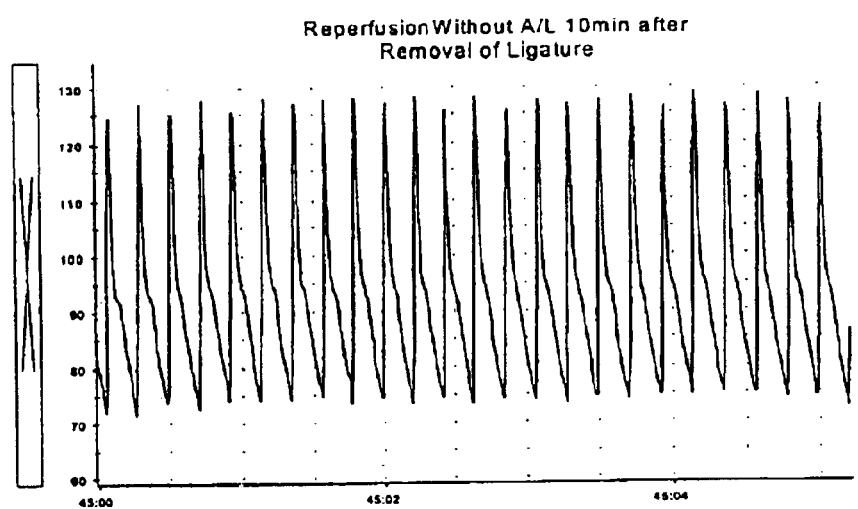
FIG. 9 is a graph showing 30 min ischaemia in rat heart in vivo following coronary artery ligation when infused with adenosine (6.3 mg/ml) and lignocaine (12.6 mg/ml) at 1 ml/hour/300 g rat.
Figure 10:
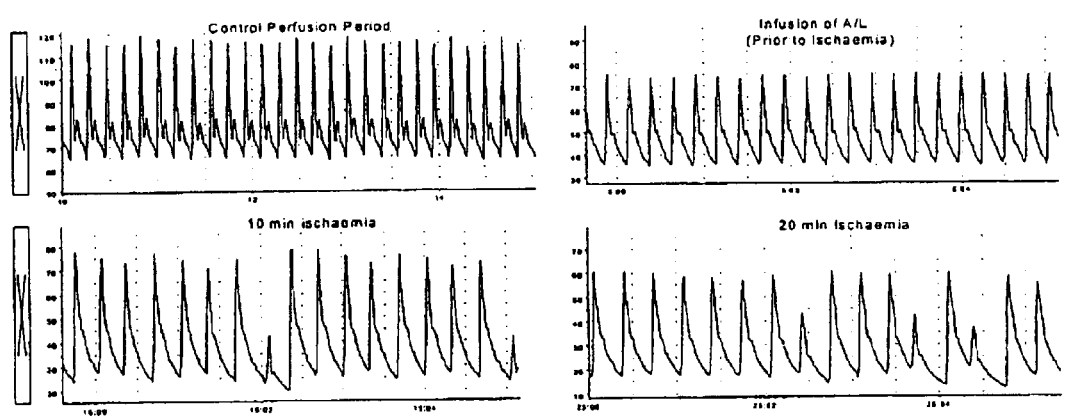
FIG. 10 is four graphs showing 20 min ischaemia in rat heart in vivo following coronary artery ligation when infused with adenosine (3.15 mg/ml) and lignocaine (12.6 mg/ml) at 1 ml/hour/300 g rat.
Figure 11:
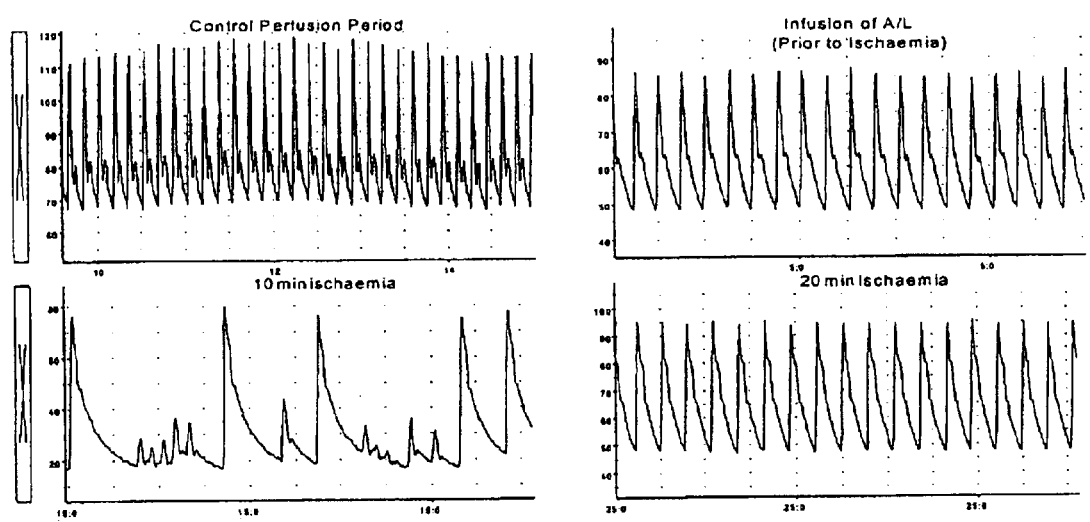
FIG. 11 is four graphs showing 300 min ischaemia in rat heart in vivo following coronary artery ligation when infused with adenosine (1.6 mg/ml) and lignocaine (12.6 mg/ml) at 1 ml/hour/300 g rat.
Figure 12:
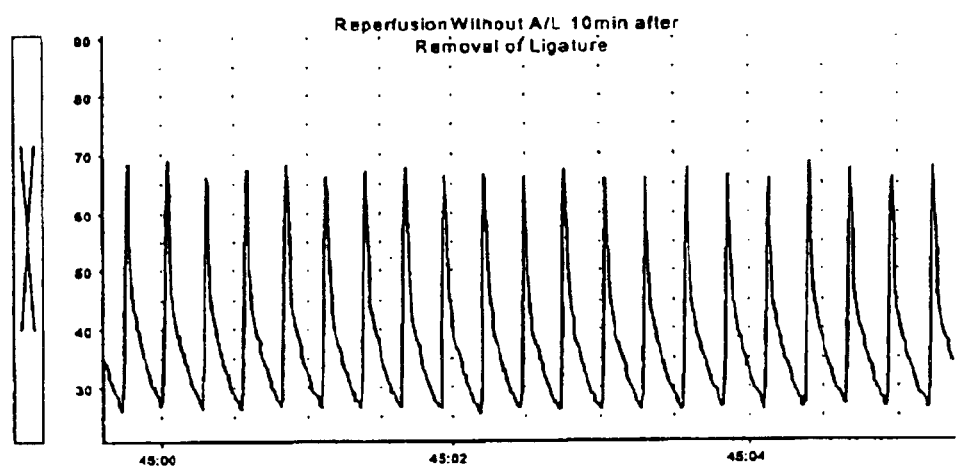
FIG. 12 is a graph showing 30 min ischaemia in rat heart in vivo following coronary artery ligation when infused with adenosine (1.6 mg/ml) and lignocaine (12.6 mg/ml) at 1 ml hour/300 g rat.

Male Wistar rats (250 g) were housed in a temperature and light-controlled room. Food and water were provided freely until the day before the experiment when the food was withheld and the rats were fasted overnight. The rats were anaesthetised with an intraperitoneal injection of pentobarbital (60 mg kg$^{-1}$). Under anaesthesia, the rats were implanted with cannulas in the femoral vein and artery for adenosine and lignocaine (AL) administration and blood pressure measurement, respectively. A tracheotomy was performed and the rats were artificially ventilated with room air at 60 to 70 breaths/min. The chests of the rats were cut open and the left anterior descending (LAD) coronary artery located. A piece of suture was placed underneath LAD. After a 20 min baseline period, LAD of the group of experimental rats were ligated for 30 min and blood pressure and heart rate monitored. After 30 min of ischaemia, the ligature was released and the heart reperfused for 20 min. In the control rats, no AL was administered as shown in FIG. 7. In the AL infusion 3 rats were used at three different doses of adenosine:

(1) 6.3 mg/ml adenosine+12.6 mg/ml lignocaine infused at 1 ml/hr/300 g rat as shown in FIGS. 8 and 9;
(2) 3.15 mg/ml adenosine+12.6 mg/ml lignocaine infused at 1 ml/hr/300 g rat as shown in FIG. 10; and
(3) 1.6 mg/ml adenosine+12.6 mg/ml lignocaine infused at 1 ml/hr/300 g rat as shown in FIGS. 11 and 12.

Compared to rats with 30 min ischaemia (no AL infusion) it was found that AL protected the heart in a dose dependent manner with the greatest protection occurring at the higher doses. As the dose of adenosine was halved, the protection was progressively lost. However, even in the worse case, the function of the heart was significantly better than with no AL alone. All hearts in rats receiving AL recovered in rate and pressure.

Summary of Adenosine and lignocaine during a Heart Attack in vivo

During a 30 min heart attack or myocardial infarction (MI) in the rat model, FIG. 7 shows that at 10 min blood pressure approaches zero and the animal would be considered close to death. After 10 min, the heart recovers and blood pressure increases and is highly erratic from the ischaemic insult. This recovery is probably due to the recruitment of collateral circulation. In contrast, when a solution of adenosine and lignocaine is infused into the rat 5 min before occluding the coronary artery, no such fall in blood pressure is seen at 10 min (FIG. 8). Where the animal without receiving AL solution nearly died at 10 min, in the presence of AL solution the heart lowers its rate of contraction and misses only a few beats. Noteworthy, there was no irregular beating of the heart at 20 min of ischaemia. All hearts recovered to full function after AL infusion was stopped (FIG. 9). It can be concluded that the heart in the presence of AL solution was dramatically protected against a profound ischaemic insult elicited by occluding the coronary artery. The protective effect of the AL solution on the heart was related to the dose of adenosine. If the amount of adenosine was halved but the amount of lignocaine remained constant, more variability at 10 min and 20 is seen (FIG. 10). If the amount of adenosine was halved again, the protection was reduced further. In all cases however, AL infused rats fully recovered haemodynamic function based on blood pressure and heart rate (FIG. 12).

Figure 13:
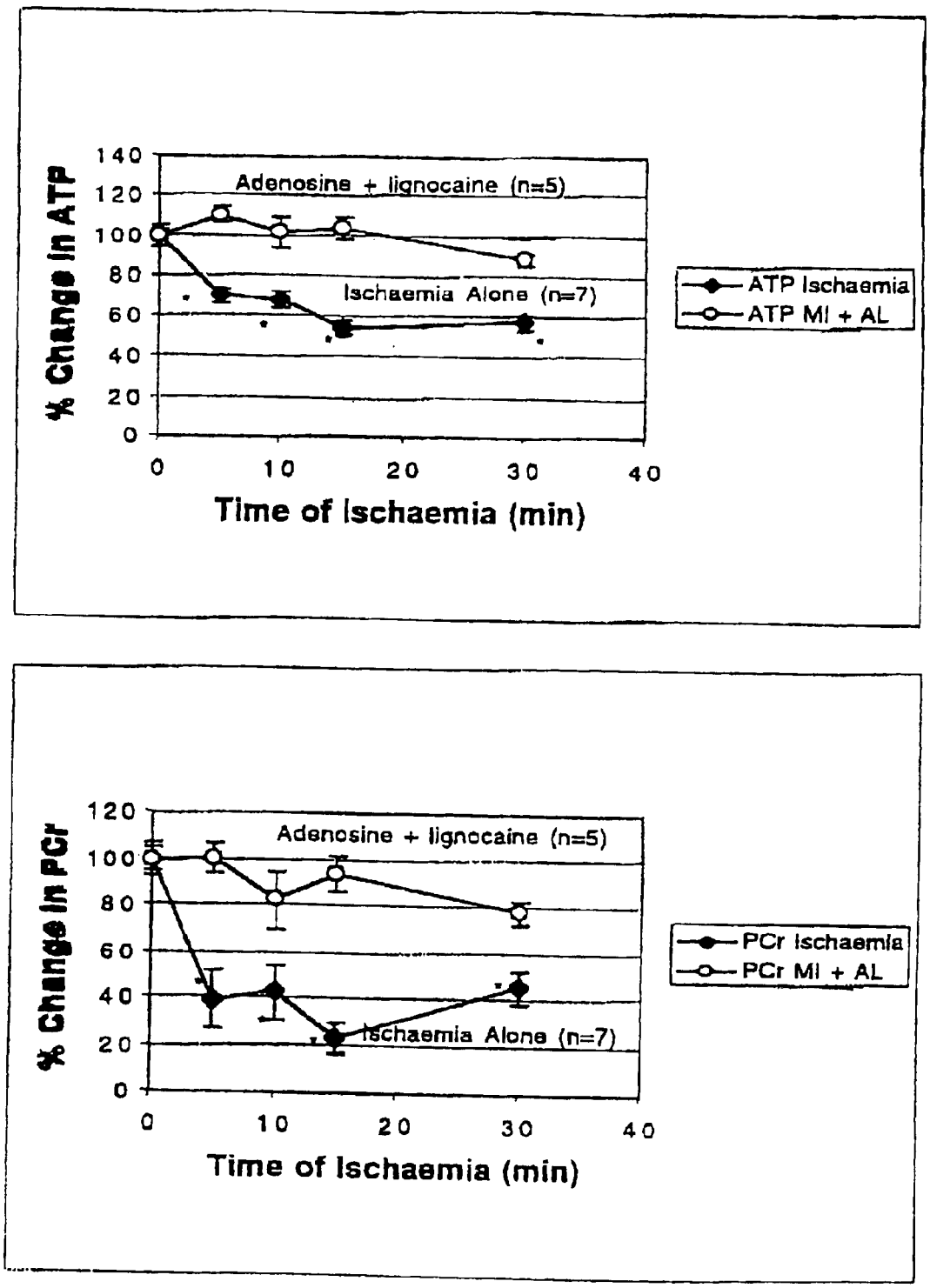
FIG. 13 is two graphs showing the change in ATP and PCr versus time of ischaemia during a heart attack in vivo with and without the presence of AL.
Figure 14:
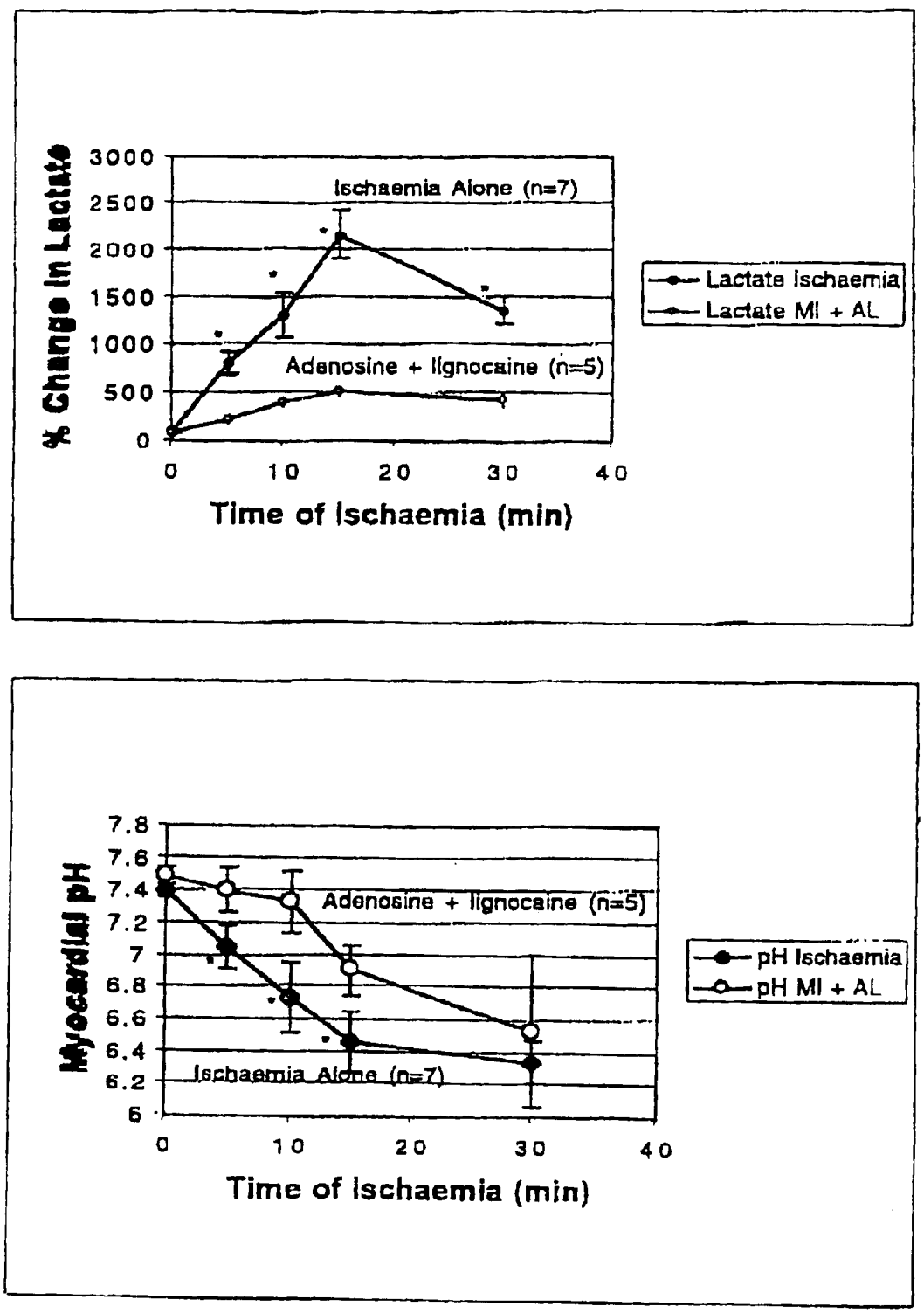
FIG. 14 is two graphs showing the change in lactate and myocardial pH versus time of ischaemia during a heart attack in vivo with and without the presence of AL.
Figure 15:
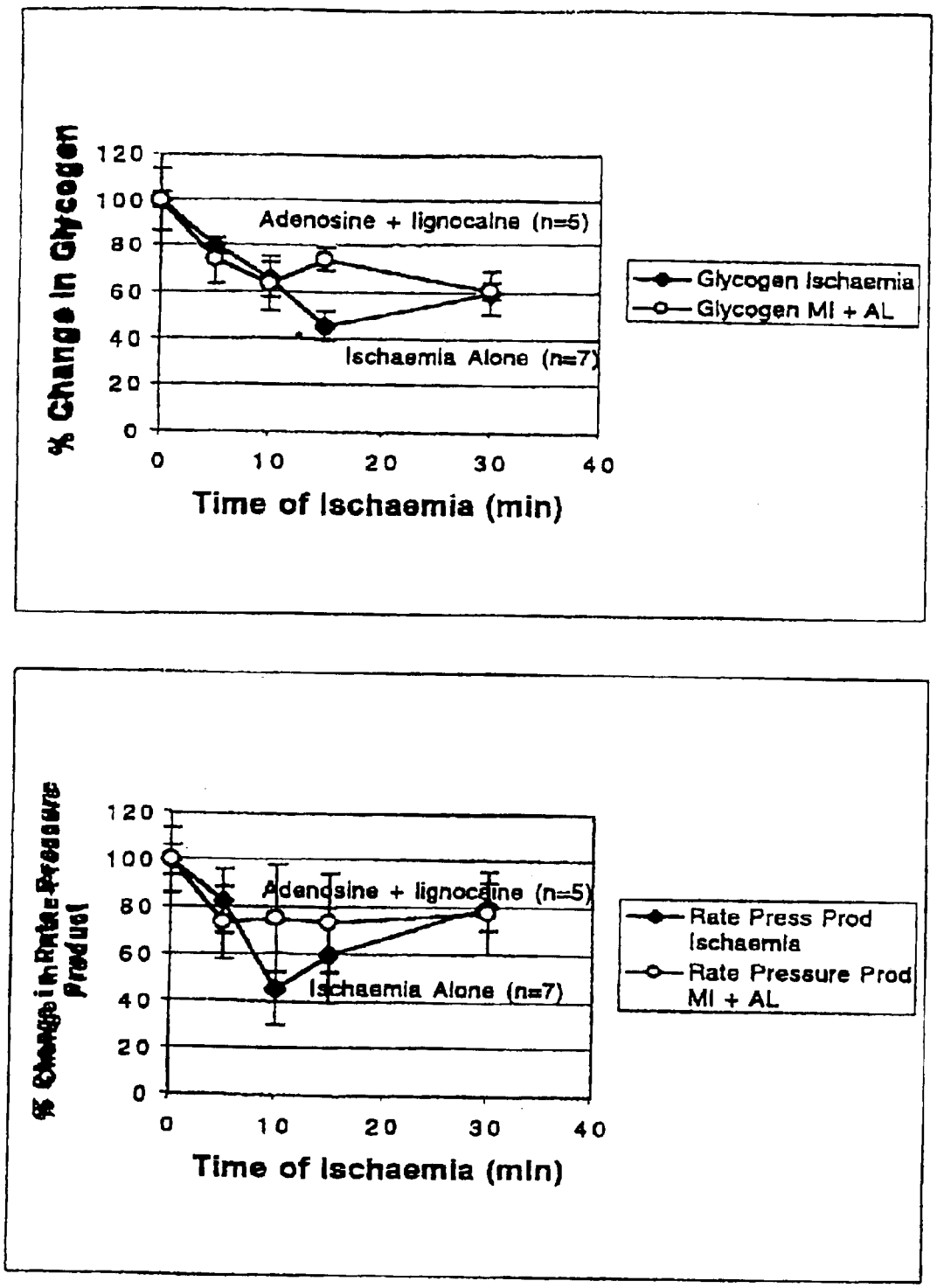
FIG. 15 is two graphs showing the change in glycogen and rate pressure product versus time of ischaemia during a heart attack in vivo with and without the presence of AL.

Two groups of rats undergoing a heart attack with and without a solution of AL were placed in a nuclear magnetic resonance (NMR) spectrometer and the metabolic data is shown in FIGS. 13 to 15. NMR non-invasively measures the changes in adenosine-triphosphate (ATP), phosphocreatine (PCr) and pH during 30 min of coronary artery occlusion. In a separate experiment on the bench, hearts were freeze-clamped at liquid nitrogen temperatures and glycogen and lactate were measured using routine enzymatic methods on neutralised tissue acid-extracts using a spectrophotometer. Major significant differences ($P<0.05$) were seen in the hearts receiving AL solution during coronary artery occlusion. ATP remained between 90–100% of the control values in AL hearts compared to 60% in hearts receiving no AL (FIG. 13). The same was shown for the high-energy phosphate store PCr, although greater percentage falls were shown in hearts with no AL (down to as low as 20% of pre-occlusion values) (FIG. 14). In hearts receiving AL over the ischaemic period lactate, an end-product of anaerobic metabolism, increased 5-fold whereas lactate in hearts without AL increased over 20-fold (FIG. 15). This was also supported by measuring the myocardial cell pH; greater decreases in pH (more acid) are seen in hearts not receiving AL solution. Noteworthy, in the first 10 min the pH fell only slight in AL hearts indicating that the myocardial cells in the presence of AL were more aerobic supported by the lower tissue lactate levels. The fuel glycogen was used in similar amounts by hearts with and without AL in the first 10 min but remained at about 60–70% of the pre-occlusion values in AL hearts compared to ischaemic hearts alone. It can be concluded from the metabolic data that coronary-occluded hearts receiving AL remained more aerobic than those hearts not receiving AL. Glycogen was a major source of fuel for each heart but the AL hearts preferentially regenerated their ATP from microchondrial oxidative phosphorylation not from lactate production. This is wholly consistent with the functional data discussed above from changes in blood pressure and heart rate.

EXAMPLE 6

Arrest solutions were made with 200 μ and 50 μM of the local anaesthetics prilocaine, procaine and mepivacaine in Krebs-Henseleit having 10 mM glucose at pH7.4. The results shown in Table 11 below are for 30 min constant perfusion of cardioplegia at 70 mmHg.

TABLE 11

|  | Adenosine + PRILOCAINE | Adenosine + PROCAINE | Adenosine + MEPIVACAINE |
|---|---|---|---|
| ARREST TIME | 13 s | 21 s | 10.5 s |
| 1st BEAT | 1:13 | 1:45 | 0:36 |
| AORTIC FLOW RECOVERY | 3:12 | 3:35 | 3:40 |
| 5 min AF % | 67% | 58% | 39% |

EXAMPLE 7

Arrest solutions were made with pinacidil dissolved in 0.05% dimethysulfoxide (DMSO) (200 $\mu$M) the local anaesthetics prilocaine, procaine, mepivacaine and lignocaine in Krebs-Henseleit solution. As shown in Table 12 below, pinacidil was found to be not as effective as adenosine.

TABLE 12

|  | Pinacidil + PRILO-CAINE | Pinacidil + PROCAINE | Pinacidil + MEPIVA-CAINE | Pinacidil + LIGNOCAINE |
|---|---|---|---|---|
| Arrest Time | 1:28 | 4:22 s | 0:41 | 1:49 |
| 1ST Beat | 2:15 | 1:20 | 0:56 | 2:30 |
| Aortic Flow Recovery | 8:10 | 4:50 | 6:55 | 4:45 |
| 5 min AF % | 0% | 25% | 0% | 70% |
| 15 min AF % | 38% | 57% | 36% | 71% |

EXAMPLE 8

The addition of the ATP-potassium channel blocker, glibenclamide (20 $\mu$M) and adenosine and lignocaine, delayed arrest times more than threefold from 26 sec (AL) to 76–120 sec (ALG) (n=2). Furthermore the slower recovery times and lower aortic flow (42–53%) in the presence of glibenclamide shows the importance of opening the KATP channels as a mode of arrest and protection afforded by AL. It can be concluded from these results that the ATP-potassium channel is an important target eliciting the arrest response from adenosine and lignocaine.

TABLE 13

|  | A/L + 20 $\mu$M Glibenclamide (n = 2) | A/L Alone (n = 5) |
|---|---|---|
| Arrest Time | 76–120 s | 26 s |
| 1st Beat | 2:45–2:55 (min:s) | 1 min:37 s |
| Aortic Flow Recovery Time | 5:00–7:30 (min:s) | 3 min:51 s |
| 5 min AF % | 42–53% | 84% |

What is claimed is:

1. A composition comprising:
   a pharmaceutically acceptable carrier;
   a compound chosen from a potassium channel opener, a potassium channel agonist and an adenosine receptor agonist; and
   a local anesthetic;
   wherein the compound and the local anesthetic are present in the composition in amounts sufficient to arrest the heart; and
   wherein the pharmaceutically acceptable carrier includes potassium at a concentration of less than about 10 mM.

2. The composition of claim 1, wherein the potassium channel opener or potassium channel agonist is selected from nicorandil, diazoxide, minoxidil, pinicadil, aprikalim, cromokulim, NS-1619 (1,3-dihydro 1-[2-hydroxy5 (trifluoromethyl)phenyl]5-(trifluoromethyl)2—H-benimidazol-one), amlodipine, Bay K 8644(L-type)(1,4-dihydro-26-dimethyl-5-nitro-4[2(trifluoromethyl)phenyl]-3-pyridine carboxylic acid (methyl ester)), bepridil HCl (L-type), calciseptine (L-type), omega-conotoxin GVIA (N-type), omega-conotoxin MVIIC(Q-type), cyproheptadine HCl, dantrolene sodium ($Ca^{2+}$ release inhibitor), diltiazem HCl (L-type), filodipine, flunarizine HCl ($Ca^{2+}/Na^{+}$), fluspirilene (L-type), HA-1077 2 HCl(1-(5isoquinolinyl sulphonyl) homo piperazine HCl), isradipine, loperamide HCl, manoalide ($Ca^{2+}$ release inhibitor), nicardipine HCl (L-type), nifedipine (L-type), niguldipine HCl (L-type), nimodipine (L-type), nitrendipine (L-type), pimozide (L- and T-type), ruthenium red, ryanodine (SR channels), taicatoxin, verapamil HCl (L-type), methoxy-verapamil HCl (L-type), YS-035 HCl (L-type)N[2(3,4 dimethoxyphenyl) ethyl]-3,4-dimethoxy N-methyl benzene ethaneamine HCl) and AV blockers.

3. The composition of claim 2, wherein the AV blocker is adenosine.

4. The composition of claim 1, wherein the adenosine receptor agonist is selected from $N^6$-cyclopentyladenosine (CPA), N-ethylcarboxamido adenosine (NECA),2-[p-(2-carboxyethyl)phenethyl-amino-5'-N-ethylcarboxamido adenosine (CGS-21680), 2-chloroadenosine, $N^6$-[2-(3,5-dimethoxyphenyl)-2-(2-methoxyphenyl]ethyladenosine, 2-chloro-$N^6$ cyclopentyladenosine (CCPA), N-(4-aminobenzyl)9-[5-(methylcarbonyl)-beta-D-robofuranosyl]-adenine (AB-MECA), ([IS-[1a,2b,3b,4a (S*)]]-4-(7-[[2-(3-chloro-2-thienyl)-1-methyl-propyl] amino]-3H-imidazole[4,5-b]pyridyl-3-yl]cyclopentane carboxamide(AMP579, $N^6$-(R)-phenylisopropyladenosine (R-PLA), aminophenylethyladenosine [9](APNEA) and cyclohexyladenosine (CHA).

5. The composition of claim 1, wherein the local anesthetic is selected from mexiletine, diphenylhydantoin, prilocaine, procaine, mepivacaine and Class 1B antiarrhythmic agents.

6. The composition of claim 5, wherein the Class 1B antiarrhythmic agents is lignocaine.

7. The composition of claim 1, wherein the pharmaceutically acceptable carrier comprises a buffer which maintains the pH of the composition in the range from about 6 to about 9.

8. The composition of claim 7, wherein the buffer is selected from the group consisting of Krebs-Henseleit, St. Thomas No. 2 solution, Tyrodes solution, Fremes solution, Hartmanns solution and Ringers-Lactate.

9. The composition of claim 1, wherein the pharmaceutically acceptable carrier comprises magnesium having a concentration of about 2.5 mM.

10. The composition of claim 1, further comprising a medicament chosen from dipyridamole and a clot-busting drug.

11. The composition of claim 10, wherein the clot-busting drug is streptokinase.

12. A method for arresting, preserving, and/or protecting an organ comprising adding or administering an effective amount of a composition according to claim 1.

13. The method of claim 12, wherein the organ is a heart either intact in the body of a subject or isolated.

14. The method of claim 13, wherein the heart is arrested during open-heart surgery.

15. A method according to claim 13, comprising arresting the heart with the composition.

16. A method according to claim 15, further comprising preserving and/or protecting the heart with the composition.

17. A method according to claim 12, wherein the potassium channel opener or potassium channel agonist is selected from nicorandil, diazoxide, minoxidil, pinicadil, aprikalim, cromokulim, NS-1619 (1,3-dihydro-1-[2-hydroxy5(trifluoromethyl)phenyl]5-(trifluoromethyl)2—H-benimidazol-one), amlodipine, Bay K 8644(L-type)(1,4-dihydro-26-dimethyl-5-nitro-4[2(trifluoromethyl)phenyl]-3-pyridine carboxylic acid (methyl ester)), bepridil HCl (L-type), calciseptine (L-type), omega-conotoxin GVIA (N-type), omega-conotoxin MVIIC(Q-type), cyproheptadine HCl, dantrolene sodium ($Ca^{2+}$ release inhibitor), diltiazem HCl (L-type), filodipine, flunarizine HCl ($Ca^{2+}/Na^+$), fluspirilene (L-type), HA-1077 2HCl(1-(5 isoquinolinyl sulphonyl) homo piperazine HCl), isradipine, loperamide HCl, manoalide ($Ca^{2+}$ release inhibitor), nicardipine HCl (L-type), nifedipine (L-type), niguldipine HCl (L-type), nimodipine (L-type), nitrendipine (L-type), pimozide (L- and T-type), ruthenium red, ryanodine (SR channels), taicatoxin, verapamil HCl (L-type), methoxy-verapamil HCl (L-type), YS-035 HCl (L-type)N[2(3,4-dimethoxyphenyl) ethyl]-3,4-dimethoxy N-methyl benzene ethaneamine HCl) and AV blockers.

18. A method according to claim 12, wherein the adenosine receptor agonist is selected from $N^6$-cyclopentyladenosine (CPA), N-ethylcarboxamido adenosine (NECA), 2-[p-(2-carboxyethyl)phenethyl-amino-5'-N-ethylcarboxamido adenosine (CGS-21680), 2-chloroadenosine, $N^6$— [2-(3,5-dimethoxyphenyl)-2-(2-methoxyphenyl]ethyladenosine, 2-chloro-N-$^6$-cyclopentyladenosine (CCPA), N-(4-aminobenzyl)-9-[5-(methylcarbonyl)-beta-D-robofuranosyl]-adenine(AB-MECA), ([IS-[1a,2b,3b,4a(S*)]]4-[7-[[2-(3-chloro-2-thienyl) 1-methyl-propyl]amino]-3H-imidazole[4,5-b] pyridyl-3-yl]cyclopentane carboxamide(AMP579, $N^6$— (R)-phenylisopropyladenosine (R-PLA), aminophenylethyladenosine [9](APNEA) and cyclohexyladenosine (CHA).

19. A method according to claim 12, wherein the local anesthetic is selected from mexiletine, diphenylhydantoin, prilocaine, procaine, mepivacaine and Class 1B antiarrhythmic agents.

20. A method according to claim 12, comprising a buffer selected from the group consisting of Krebs-Henseleit, St. Thomas No. 2 solution, Tyrodes solution, Fremes solution, Hartmanns solution and Ringers-Lactate.

21. A method according to claim 12, the composition further comprising a medicament chosen from dipyridamole and a clot-busting drug.

* * * * *